US010844046B2

(12) United States Patent
Hogendorf et al.

(10) Patent No.: US 10,844,046 B2
(45) Date of Patent: Nov. 24, 2020

(54) IMIDAZOLYL-SUBSTITUTED INDOLE DERIVATIVES BINDING 5-HT7 SEROTONIN RECEPTOR AND PHARMACEUTICAL COMPOSITIONS THEREOF

(71) Applicant: INSTYTUT FARMAKOLOGII POLSKIEJ AKADEMII NAUK, Cracow (PL)

(72) Inventors: Adam Hogendorf, Cracow (PL); Agata Hogendorf, Cracow (PL); Grzegorz Satala, Cracow (PL); Rafal Kurczab, Tarnow (PL); Ryszard Bugno, Cracow (PL); Jakub Staron, Cracow (PL); Tomasz Lenda, Cracow (PL); Andrzej J Bojarski, Zabierzow (PL)

(73) Assignee: INSTYTUT FARMAKOLOGII POLSKIEJ AKADEMII NAUK, Cracow (PL)

( * ) Notice: Subject to any disclaimer, the term of this patent is extended or adjusted under 35 U.S.C. 154(b) by 0 days.

(21) Appl. No.: 16/318,794

(22) PCT Filed: Jul. 21, 2017

(86) PCT No.: PCT/EP2017/068531
§ 371 (c)(1),
(2) Date: Jan. 18, 2019

(87) PCT Pub. No.: WO2018/015558
PCT Pub. Date: Jan. 25, 2018

(65) Prior Publication Data
US 2019/0284169 A1 Sep. 19, 2019

(30) Foreign Application Priority Data

Jul. 21, 2016 (PL) ................................. 16461543.7

(51) Int. Cl.
*C07D 403/04* (2006.01)
(52) U.S. Cl.
CPC .................................. *C07D 403/04* (2013.01)
(58) Field of Classification Search
CPC .................................................. C07D 403/04
See application file for complete search history.

(56) References Cited

U.S. PATENT DOCUMENTS 6,699,883 B1  3/2004 Doemling

FOREIGN PATENT DOCUMENTS

| WO | 96/03388 A1 | 2/1996 |
| WO | 01/46178 A2 | 6/2001 |
| WO | 2008/119741 A2 | 10/2008 |

OTHER PUBLICATIONS

Chemical Abstracts Registry No. 27419-69-8, indexed in the Registry file on STN CAS Online Nov. 16, 1984. (Year: 1984).*
Beck et al., QSAR & Combinatorial Science, (2006), 25(5-6), pp. 527-535. (Year: 2006).*
Aghajanian et al., Serotonin, Neuropsychopharmacology, pp. 15-34 (2002).
Ruat et al., Molecular cloning, characterization, and localization of a high-affinity serotonin receptor (5-HT7) activating cAMP formation, Proc. Natl. Acad. Sci, USA, 90:8547-8551 (1993).
Lovenberg et al., A novel adenylyl cyclase-activating serotonnin receptor (5-HT7) implicated in the regulation of mammalian circadian rhythms, Neuron, 11:449-458 (1993).
Bard et al., Cloning of a Novel Human Serotonin Receptor (5-HT7) Positively Linked to Adenylate Cyclase, The Journal of Biological Chemistry, 268(31):23422-23426 (1993).
Hedlund et al., Functional, molecular and pharmacological advances in 5-HT7 receptor research, TRENDS in Pharmacological Sciences, 25(9):481-486 (2004).
Naumenko et al., Interplay between Serotonin 5-HT1A and 5-HT7 Receptors in Depressive Disorders, CNS Neuroscience & Therapeutics, 20:582-590 (2014).
Roberts et al., Mice lacking 5-HT7 receptors show specific impairments in contextual learning, European Journal of Neuroscience, 19:1913-1922 (2004).
Gasbarri et al. Effect of 5-HT7 antagonist SB-269970 in the modulation of working and reference memory in the rat, Behavioural Brain Research, 195:164-170 (2008).
Eriksson et al., 5-HT7 receptor stimulation by 8-OH-DPAT counteracts the impairing effect of 5-HT1A receptor stimulation on contextual learning in mice, European Journal of Pharmacology, 596:107-110 (2008).
Sarkisyan et al., the 5-HT7 receptor is involved in allocentric spatial memory information processing, Behavioural Brain Research, 202:26-31 (2009).
Meneses et al., The effects of the 5-HT6 receptor agonist EMD and the 5-HT7 receptor agonist AS19 on memory formation, Behavioural Brain Research, 195:112-119 (2008).
Matthys et al., Role of the 5-HT7 Receptor in the Central Nervous System:from Current Status to Future Perspectives, Mol Neurobiol, 43:228-253 (2011).
Di Pilato et al., Selective agonists for serotonin 7 (5-HT7) receptor and their applications in preclinical models: an overview, Rev. Neurosci., 25(3):401-415 (2014).
Bento et al., The ChEMBL bioactivity database: an update, 14:D1083-D1090 (2014).

(Continued)

*Primary Examiner* — Laura L Stockton
(74) *Attorney, Agent, or Firm* — Browdy and Neimark, PLLC

(57) ABSTRACT

The invention relates to a new class of substituted indole derivatives that are able to activate 5-HT$_7$ serotonin receptor. These compounds bind 5-HT$_7$ serotonin receptor with high affinity and selectivity, while possessing favourable physicochemical properties. The compounds of the invention are the first described low-basicity 5-HT$_7$ receptor agonists. The invention also relates to use of such compounds in the treatment or prevention of 5-HT$_7$ receptor-related disorders, especially of the central nervous system. The invention also relates to the isotopically labelled compounds for use in the in vivo diagnostics or imaging of a 5-HT$_7$ serotonin receptor.

9 Claims, No Drawings

(56) References Cited

OTHER PUBLICATIONS

Sleight et al., Identification of 5-Hydorxytryptamine7 receptor binding sites in rat hypothalamus: sensitivity to chronic antidepressant treatment, The American Society for Pharmacology and Experiments Therapeutics, 47:99-103 (1995).
Mnie-Filali et al., 5-HT7 Receptor Antagonists as a New Class of Antidepressants, Drug News Prespect, 20(10):1-6 (2007).
Hagan et al., Characterization of SB-269970-A, a selective 5-HT7 receptor antagonist, British Journal of Pharmacology, 130:539-548 (2000).
Shaprio et al., Aripiprazole, A Novel Atypical Antipsychotic Drug with a Unique and Robust Pharmacology, Neuropsychopharmacology, 28:1400-141 (2003).
Brenchat et al., 5-HT7 receptor activation inhibits mechanical hypersensitivity secondary to capsaicin sensitization in Mice, PAIN, 141:239-247 (2009).
Thomson et al., Thiazoles and thiopyridines: novel series of high affinity h5HT7 ligands, Biooranic & Medicinal Chemistry Letters, 14:677-680 (2004).
Leopoldo et al., Structure-Activity Relationship Study on N-(1,2,3,4-Tetrahydronaphthalen-1-yl)-4-aryl-1-piperazinehexanamides, a Class of 5-HT7 Receptor Agents. 2, J. Med. Chem., 50:4214-4221 (2007).
Leopoldo et al., Structure-Affinity Relationship Study on N-(1,2,3,4-Tetrahydronaphthalen-1-yl)-4-Aryl-1- Piperazinealkylamides, a New Class of 5-Hydroxytryptamine? Receptor Agents, J. Med. Chem., 47:6616-6624 (2004).
Leopoldo et al., Structural Modifications of N-(1,2,3,4-Tetrahydronaphthalen-1-yl)-4-Aryl-1-piperazinehexanamides: Influence on Lipophilicity and 5-HT7 Receptor Activity. Part III, J. Med. Chem., 51:5813-5822 (2008).
Hedlund et al., LP-211 is a brain penetrant selective agonist for the serotonin 5-HT7 receptor, Neuroscience Letters, 481:12-16 (2010).
Powell et al., In Vitro Serotonergic Activity of Black Cohosh and Identification of Nω-Methylserotonin as a Potential Active Constituent, J. Agric. Food Chem., 56:11718-11726 (2008).
Bosker et al., Antagonism of 5-HT1A receptors unceovers an exitatory effect of SSRIs o 5-HT neuronal activity, an action probably mediated by 5-HT7 receptors, Journal of Neurochemistry, 108:1126-1135 (2009).
Tiwari et al., Design, synthesis and biological evaluation of small molecule-based PET radioligands for the 5-hydroxytryptamine 7 receptor, RSC Adv., 5:19752-19759 (2015).
Canese et al., Persistent modification of forebrain networks and metabolism in rats following adolescent exposure to a 5-HT7 receptor agonist, Psychopharmacology, DOI 10.1007/s00213-014-3639-6 (2014).
De Filippis et al., Long-lasting beneficial effects of central serotonin receptor 7 stimulation in female mice modeling Rett syndrome, Frontiers in Behavioral Neuroscience, 9(96):1-11 (2015).
Costa et al., Activation of 5-HT7 Serotonin Receptors Reverses Metabotropic Glutamate Receptor-Mediated Synaptic Plasticity in Wild-Type and Fmr1 Knockout Mice, a Model of Fragile X Syndrome, Biol Psychiatry, 72:924-933 (2012).
Clark et al., Halogen bonding: the σ-hole, J M Moel, 13:291-29 (2007).
Clark, σ-Holes, John Wiley & Sons, Ltd., 00:1-8 (2012).
Wilcken et al., Principles and Applications of Halogen Bonding in Medicinal Chemistry and Chemical Biology, Journal of Medicinal Chemistry, pp. A-Z (2012).
Agarwal et al., A New Synthesis of the Potent 5-HT1 Receptor Ligand, 5-Carboxyamidotryptamine (5-CT), Synthetic Communications, 23(8):1101-1110 (1993).
Cheng et al., Relationship Between the Inhibition Constant (K1) and the Concentration of Inhibitor Which Causes 50 Per Cent Inhibition (I50) of an Enzymatic Reaction*, Biochemical Pharmacology, 22:3099-3108 (1973).
Zajdel et al., The multiobjective based design, synthesis and evaluation of the arylsulfonamide/amide derivatives of aryloxyethyl- and arylthioethyl-piperidines and pyrrolidines as a novel class of potent 5-HT7 receptor antagonists, European Journal of Medicinal Chemistry, 56:348-360 (2012).
Deau et al., Rational Design, Pharmacomodulation, and Synthesis of Dual 5-Hydroxytryptamine 7 (5-HT7)/5-Hydroxytryptamine 2A (5-HT2A) Receptor Antagonists and Evaluation by [18F]-PET Imaging in a Primate Brain, Journal of Medicinal Chemistry, 58:8066-8096 (2015).
Greengrass et al., Binding Characteristics of 3H-Prazosin to Rat Brain a-Adrenergic Receptors, European Journal of Pharmacology, 55:323-326 (1979).
Devedijian et al., Further characterization of human a2-adrenoceptor subtypes:[3H]RX821002 binding and definition of additional selective drugs, European Journal of Pharmacology, 252:4349 (1994).
Rinaldi-Carmona et al., characterization of two cloned human CB1 cannabinoid receptor isoforms, The Journal of Pharmacology and Experiment Therapeutics, 278(2):871-878 (2019).
MacKenzie et al., Characterization of the human dopamine D3 receptor expressed in transfected cell lines, European Journal of Pharmacology, 266:79-85 (1994).
Smit et al., Regulation of the human histamine H1 receptor stably expressed in Chinese hamster ovary cells, British Journal of Pharmacology, 117:1071-1080 (1996).
Hoyer et al., Characterization of the 5-HT1a Recognition Site in Rat Brain: Binding Studies With ( −)[125I]Iodocyanopindolol, European Journal of Pharmacology, 118:1-12 (1985).
Choi et al., The human serotonin 5-HT2B receptor: pharmacological link between 5-HT2 and 5-HT1D receptors, FEBS Letters, 352:393-399 (1994).
Rees et al., Cloning and characterisation of the human 5-HT,* serotonin receptor, FEBS Letters, 355:242-246 (1994).
Wager et al., Moving beyond Rules: The Development of a Central Nervous System Multiparameter Optimization (CNSMPO) Approach to Enable Alignment of Druglike Properties, ACS Chemical Neuroscience, 1:435-449 (2010).
Barnes et al., Neuronal 5-HT Receptors and SERT, TOCRISH Bioscience, pp. 1-15 (2011).
Leopoldo et al., 5-HT7 receptor modulators: a medicinal chemistry survey of recent patent literature (2004-2009), Expert Opin. Ther. Patents, pp. 739-754 (2010).
Pai et al., The type 7 serotonin receptor, 5-HT 7, Is essential in the mammary gland for regulation of mammary epithelial structure and function, Biomed Research International, 242(1):285-298 (2015).
Suvorov et al., Indole derivites. LXI. Synthesis of 4(5)-(3-indolyl)imidazole, chemical abstracts services, XP002765919(2017).
Yoshida et al., Synthesis of granulatimide positional analogues, Chemical and Pharmaceutical Bulletin, 51(2)209-214 (2003).
Tan et al., Suzuki-Miyaura cross-coupling reactions of unprotected haloimidazoles, The Journal of Organic Chemistry, 79(18):5873 (2014).

* cited by examiner

IMIDAZOLYL-SUBSTITUTED INDOLE DERIVATIVES BINDING 5-HT7 SEROTONIN RECEPTOR AND PHARMACEUTICAL COMPOSITIONS THEREOF

The invention relates to a new class of compounds able to activate 5-HT$_7$ serotonin receptor. These compounds bind 5-HT$_7$ serotonin receptor with high affinity and selectivity. The invention also relates to such compounds for use of in the treatment or prevention of 5-HT$_7$ receptor-related disorders, especially of the central nervous system. The invention also relates to the isotopically labelled compounds for use in the in vivo diagnostics or imaging of a 5-HT$_7$ serotonin receptor.

BACKGROUND OF THE INVENTION

Serotonin is one of the most important neurotransmitters involved in numerous physiological processes such as thermoregulation, sleep, regulation of appetite, sex, mood, memory formation, cognition, vision, functioning of digestive system.[1] Fourteen to-date identified serotonin receptors have been assigned to seven families. Since its discovery in 1993,[2-4] 5-HT$_7$ receptor has been recognized as potential therapeutic target regarding numerous disorders. The receptor is involved in thermoregulation, vasoconstriction,[5,6] learning and memory formation,[7-11] sleep, mood, and circadian rhythm.[12] Animal models suggest the role of 5-HT$_7$R in aetiology of mood disorders (e.g. depression), gut disorders, anxiety, and pain.[13,14] Several drugs that are currently used for the treatment of CNS disorders including antipsychotics: aripiprazole, amisulpride, chlorpromazine, clozapine, risperidone, ziprasidone are 5-HT$_7$R active. (Binding affinities of antipsychotics were measured in radioligand displacement assays in our laboratory; the results are consistent with data from, e.g., ChEMBL database, ebi.ac.uk/chembl/).[15] There is evidence that 5-HT$_7$R localized in hypothalamus downregulates in response to treatment with the antidepressant fluoxetine.[16] 5-HT$_7$R antagonists have been proposed as novel generation antidepressants.[16] Known 5-HT$_7$ receptor agonists include 5-CT, 5-methoxytryptamine, 8-OH-DPAT,[18] aripiprazole (weak partial agonist),[19] AS-19, E-55888,[20] MSD-5a,[20,21] LP-12,[22] LP-44,[23] LP-211,[24] $^{RA}$-7,[25] N$^\omega$methylserotonin.[26] A truly selective agonist for the 5-HT$_7$ receptor is not available. The most frequently used candidate is AS-19, but a recent binding profile showed that it has affinity also for other receptors.[27] Lack of selective, high affinity agonists of 5-HT$_7$R implicates the absence of a successful agonist PET-radioligand.[28] Animal models suggest several possible indications of 5-HT$_7$R agonists as therapeutics. Stimulation of 5-HT$_7$R in adolescent rats by LP-211 causes plastic rearrangements within forebrain networks, accounting for long-lasting behavioural changes in the adulthood.[29] Activation of 5-HT$_7$R was found beneficial in mouse model of Rett syndrome[30] and Fragile X syndrome.[31]

U.S. Pat. No. 6,699,883 discloses various 3-pyrroloimidazole derivatives to be used for the treatment of tumours and cancers, and also as antibiotics, especially antibacterial ones.

SUMMARY OF THE INVENTION

The present invention relates to a new class of compounds able to activate 5-HT$_7$ receptor. The inventive compounds bind to 5-HT$_7$ receptor with high affinity and selectivity. The invention also relates to such compounds for use in the treatment or prevention of 5-HT$_7$ receptor-related disorders, especially of the central nervous system.

The described compounds exhibit very desired physicochemical parameters, including low molecular mass, optimal calculated log P, optimal topological polar surface area (TPSA), and a small number of hydrogen bond donors. The described compounds are first known low-basicity 5-HT$_7$ receptor agonists. The examples of low-basicity agonists of aminergic (e. g. serotonin, dopamine, histamine, adrenergic) receptors are extremely scarce. The presented invention can bring useful insights into both G protein-coupled receptors and low-basicity aminergic receptor ligands research. For each compound, the CNS MPO (Multi Parameter Optimization) parameter was calculated based on calculated log P. The high activity at 5-HT$_7$ receptor and very high selectivity over related CNS targets, taken together with high CNS MPO scores, the exceptional ease of synthesis, and the ease of introduction of isotopically labelled substrates during synthesis anticipate a very high potential to be used as pharmaceutical drugs or molecular probes for both in-vitro and in-vivo experiments.

In one aspect, the invention concerns a substituted indole derivative of Formula (I),

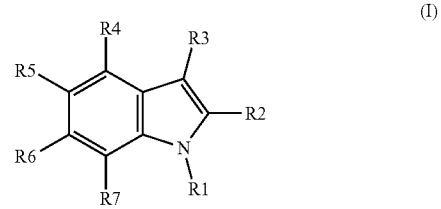

(I)

wherein:
R1 represents hydrogen or C$_1$-C$_2$ alkyl;
R4 represents hydrogen, halogen, C$_1$-C$_4$ alkyl, C$_1$-C$_4$ alkoxy, or an electron-withdrawing group;
R7 represents hydrogen, halogen, C$_1$-C$_2$ alkyl, or an electron-withdrawing group;
exactly one of the substituents R2, R3, R5, and R6 is a substituted imidazol-5-yl of Formula (II)

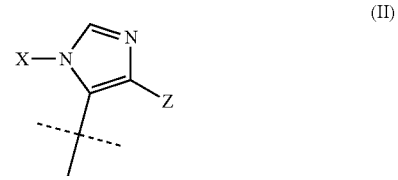

(II)

wherein:
X represents hydrogen, C$_1$-C$_6$ alkyl, C$_3$-C$_6$ cycloalkyl, C$_2$-C$_4$ alkenyl, C$_1$-C$_4$ alkoxy, methoxy-C$_1$-C$_6$ alkyl, C$_6$-C$_{10}$ aryl, C$_6$-C$_{10}$ aryl-C$_1$-C$_4$ alkyl, C$_3$-C$_9$ heteroaryl, or C$_3$-C$_9$ heteroaryl-C$_1$-C$_4$ alkyl; and
Z represents hydrogen or C$_1$-C$_6$ alkyl;
and the remaining substituents R2, R3, R5, and R6 represent the following values:
R2 represents hydrogen or C$_1$-C$_2$ alkyl;
R3 represents hydrogen;
R5 represents hydrogen, halogen, C$_1$-C$_6$ alkyl, hydroxy, C$_1$-C$_6$ alkoxy, benzyloxy, cyano, or an electron-withdrawing group;

R6 represents hydrogen, halogen, $C_1$-$C_2$ alkyl, or an electron-withdrawing group; wherein the halogen can be selected from fluorine, chlorine, bromine, and iodine; wherein the electron-withdrawing group can be selected from $NO_2$, $CF_3$, $CF_2CF_3$, $CH_2CF_3$, $CH_2CHF_2$, $CH_2CH_2F$, $COOCH_3$, $CONH_2$, $SO_2CH_3$ and $SO_2NH_2$;

or its isomers, mixtures of isomers in any proportions, tautomers, solvates including hydrates, or pharmaceutically acceptable salts thereof, for use in the treatment of a disease or disorder mediated by 5-$HT_7$ serotonin receptor.

It is understood that a subject suffering from a disease or disorder mediated by 5-$HT_7$ serotonin receptor can benefit from the treatment with the compound of the invention capable to selectively bind that 5-$HT_7$ serotonin receptor.

In particular, the compound of the invention can be used in the treatment or prevention of a disease or disorder selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders.

It is possible to introduce $^{11}C$ isotope to some of the described compounds in a very concise manner; the synthetic pathway has been successfully tested on non-radioactive chemicals. $^{11}C$ labelled agonists could be used as PET-radioligands suitable for in vivo experiments. There is potential to label some of the compounds in the series with radioactive isotopes thus producing radioligands for in vitro studies.

Thus, the invention also relates to the compound of the invention, being isotopically labelled for use in the in vivo diagnostics or imaging of 5-$HT_7$ serotonin receptor.

The invention also relates to a pharmaceutical composition comprising a therapeutically effective amount of one or more compounds of the invention and one or more pharmaceutical excipients, for use in the treatment or prevention of a disease or disorder selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders.

The invention also relates to a method of treating a disease or disorder in a mammal, wherein the disease or disorder is selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders, the method comprising administering to said mammal a therapeutically effective amount of a compound of the invention.

DETAILED DESCRIPTION OF THE INVENTION

Unless otherwise stated, the following terms used in the specification and claims have the meanings given below:

The term "alkyl", such as $C_1$-$C_2$ alkyl, $C_1$-$C_4$ alkyl or $C_1$-$C_6$ alkyl, denotes a straight-chain or branched hydrocarbon radical comprising the indicated number of carbon atoms, containing no unsaturation, and attached to the rest of the molecule by a single bond. Exemplary alkyl groups include methyl, ethyl, n-propyl, isopropyl, and the like.

The term "$C_2$-$C_4$ alkenyl" denotes a straight-chain or branched hydrocarbon group comprising the indicated number of carbon atoms, containing one carbon-carbon double bond, and attached to the rest of the molecule by a single bond. Exemplary $C_2$-$C_4$ alkenyl groups include ethenyl, prop-1-enyl, prop-2-enyl, and 2-methylprop-1-enyl.

The term "$C_3$-$C_6$ cycloalkyl" denotes a cyclic hydrocarbon group comprising the indicated number of carbon atoms, containing no unsaturation, and attached to the rest of the molecule by a single bond. Exemplary $C_3$-$C_6$ cycloalkyl groups include cyclopropyl, cyclobutyl, cyclopentyl, and cyclohexyl.

The term "alkoxy", such as $C_1$-$C_4$ alkoxy or $C_1$-$C_6$ alkoxy, means an alkyl group attached via an oxygen linkage to the rest of the molecule. Exemplary alkoxy groups include methoxy, ethoxy, propyloxy, isopropyloxy, and the like.

The term "halogen" means fluorine, chlorine, bromine or iodine.

The term "$C_6$-$C_{10}$ aryl" means a monocyclic or bicyclic aromatic hydrocarbon group comprising the indicated number of carbon atoms as the ring members. Exemplary aryl groups include phenyl and naphthyl.

The term "$C_6$-$C_{10}$ aryl-$C_1$-$C_4$ alkyl" denotes a $C_6$-$C_{10}$ aryl attached via $C_1$-$C_4$ alkyl to the rest of the molecule. Exemplary $C_6$-$C_{10}$ aryl-$C_1$-$C_4$ alkyl groups include benzyl (i.e., phenylmethyl) and phenethyl.

The term "$C_3$-$C_9$ heteroaryl" means a monocyclic or bicyclic aromatic group comprising sulphur, oxygen, or nitrogen atom(s) in addition to carbon atoms as the ring members; these additional atoms may occur more than once in the ring. These rings may be either simple aromatic rings. Exemplary heteroaryl groups include pyridine, pyrimidine, benzofuranyl, benzothiophene, furyl, dioxalanyl, pyrrolyl, oxazolyl, pyridyl, pyridazinyl, pyrimidinyl, pyrazinyl, quinolinyl, indolyl and the like.

The term "$C_3$-$C_9$ heteroaryl-$C_1$-$C_4$ alkyl" denotes a $C_3$-$C_9$ heteroaryl attached via $C_1$-$C_4$ alkyl to the rest of the molecule. Exemplary $C_3$-$C_9$ heteroaryl-$C_1$-$C_4$ alkyl groups include 2-pyridymethyl and 3-pyridylmethyl.

The term "methoxy-$C_1$-$C_4$ alkyl" denotes methyl group attached via an oxygen linkage to $C_1$-$C_4$ alkyl being attached itself to the rest of the molecule. Exemplary "methoxy-$C_1$-$C_4$ alkyl" groups include methoxymethyl and 3-methoxypropyl.

The term "electron-withdrawing group" denotes any functional group diminishing the electron density at the moiety attached thereto. In this specification, the electron-withdrawing group can be selected from $NO_2$, $CF_3$, $CF_2CF_3$, $CH_2CF_3$, $CH_2CHF_2$, $CH_2CH_2F$, $COOCH_3$, $CONH_2$, $SO_2CH_3$ and $SO_2NH_2$.

The term "amido" denotes —$CONH_2$.

The term "hydroxy" denotes —OH.

The term "cyano" denotes —CN.

The term "benzyloxy" denotes benzyl, as defined above, being attached via an oxygen linkage to the rest of the molecule.

In the first aspect, the invention concerns a substituted indole derivative of Formula (I),

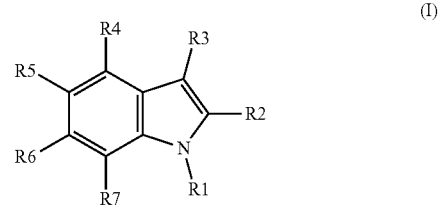

wherein:
R1 represents hydrogen or $C_1$-$C_2$ alkyl;
R4 represents hydrogen, halogen, $C_1$-$C_4$ alkyl, $C_1$-$C_4$ alkoxy, or an electron-withdrawing group;
R7 represents hydrogen, halogen, $C_1$-$C_2$ alkyl, or an electron-withdrawing group;
exactly one of the substituents R2, R3, R5, and R6 is a substituted imidazol-5-yl of Formula (II)

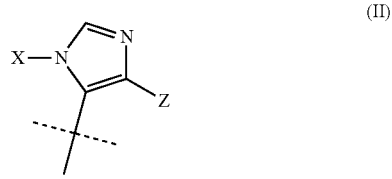

(II)

wherein:
X represents hydrogen, $C_1$-$C_6$ alkyl, $C_3$-$C_6$ cycloalkyl, $C_2$-$C_4$ alkenyl, $C_1$-$C_4$ alkoxy, methoxy-$C_1$-$C_4$ alkyl, $C_6$-$C_{10}$ aryl, $C_6$-$C_{10}$ aryl-$C_1$-$C_4$ alkyl, $C_3$-$C_9$ heteroaryl, or $C_3$-$C_9$ heteroaryl-$C_1$-$C_4$ alkyl; and
Z represents hydrogen or $C_1$-$C_6$ alkyl;
and the remaining substituents R2, R3, R5, and R6 represent the following values:
R2 represents hydrogen or $C_1$-$C_2$ alkyl;
R3 represents hydrogen;
R5 represents hydrogen, halogen, $C_1$-$C_6$ alkyl, hydroxy, $C_1$-$C_6$ alkoxy, benzyloxy, cyano, or an electron-withdrawing group;
R6 represents hydrogen, halogen, $C_1$-$C_2$ alkyl, or an electron-withdrawing group;
wherein the halogen can be selected from fluorine, chlorine, bromine, and iodine;
wherein the electron-withdrawing group can be selected from $NO_2$, $CF_3$, $CF_2CF_3$, $CH_2CF_3$, $CH_2CHF_2$, $CH_2CH_2F$, $COOCH_3$, $CONH_2$, $SO_2CH_3$ and $SO_2NH_2$;
or its isomers, mixtures of isomers in any proportions, tautomers, solvates including hydrates, or pharmaceutically acceptable salts thereof,
for use in the treatment of a disease or disorder mediated by 5-$HT_7$ serotonin receptor.

The synthetic approach to the inventive compounds of Formula (I) is discussed below.

Certain inventive compounds of Formula (I) may exist in particular geometric or stereoisomeric forms. In addition, compounds of the present invention may also be optically active. The present invention contemplates all such compounds, including cis- and trans-isomers, (R)- and (S)-enantiomers, diastereoisomers, the tautomeric forms thereof, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "racemic mixture" refers to a mixture containing equal proportions of the first enantiomer of the molecule and of the second enantiomer of this molecule, wherein the second enantiomer is the mirror image of the first one. The term "scalemic mixture" refers to any non-racemic mixture of stereoisomers of the molecule.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Organic compounds frequently occur in more than one crystalline forms, that can differ in their physical and biological properties, such as melting point, stability, solubility, bioavailability. Such crystalline forms are termed polymorphs. All polymorphs of the inventive compounds of Formula (I) and of their salts are intended to be within the scope of this invention.

The salts, hydrates, and solvates of the compounds of the invention are preferably pharmaceutically acceptable salts, hydrates, and solvates. The solvates may contain a stoichiometric or non-stoichiometric amount of one or more solvents, such as water, ethanol, or ethyl acetate, in addition to the molecule of the compound of the invention. The solvates formed with water are called hydrates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

In the preferred embodiment, the values of the substituents in Formula (I) are as follows:
R1 represents hydrogen;
R2 represents hydrogen;
R3 represents the substituted imidazol-5-yl of Formula (II) as defined above, wherein:
X represents hydrogen, $C_1$-$C_6$ alkyl, $C_3$-$C_6$ cycloalkyl, $C_2$-$C_4$ alkenyl, $C_1$-$C_4$ alkoxy, methoxy-$C_1$-$C_4$ alkyl, $C_6$-$C_{10}$ aryl, or $C_6$-$C_{10}$ aryl-$C_1$-$C_4$ alkyl; and
Z represents hydrogen;
R4 represents hydrogen, bromine, or methoxy;
R5 represents hydrogen, halogen, methyl, hydroxy, methoxy, benzyloxy, cyano, or amido;
R6 represents hydrogen or bromine;
R7 represents hydrogen, fluorine, or methyl.

In another preferred embodiment, the values of the substituents in Formula (I) are as follows:
R1 represents hydrogen or methyl;
R4 represents hydrogen, bromine, or methoxy;
R7 represents hydrogen, fluorine, or methyl;

exactly one of the substituents R2, R3, R5, and R6 is the substituted imidazol-5-yl of Formula (II) as defined above, wherein:
X represents hydrogen, methyl, ethyl, propyl, butyl, cyclopropyl, 2-propenyl, benzyl, 3-methoxypropyl, or phenethyl; and
Z represents hydrogen;
and the remaining substituents R2, R3, R5, and R6 represent the following values:
R2 represents hydrogen or methyl;
R3 represents hydrogen;
R5 represents hydrogen, halogen, methyl, hydroxy, methoxy, benzyloxy, cyano, or amido;
R6 represents hydrogen or bromine.

The preferred compounds according to the invention are as follows:
3-(1-methyl-1H-imidazol-5-yl)-1H-indole;
5-methoxy-3-(1-methyl-1H-imidazol-5-yl)-1H-indole;
3-(1-ethyl-1H-imidazol-5-yl)-1-methyl-1H-indole;
3-(1-ethyl-1H-imidazol-5-yl)-5-methoxy-1H-indole;
3-(1-propyl-1H-imidazol-5-yl)-5-methoxy-1H-indole;
3-(1-butyl-1H-imidazol-5-yl)-5-methoxy-1H-indole;
3-(1-cyclopropyl-1H-imidazol-5-yl)-5-methoxy-1H-indole;
5-methoxy-3-[1-(prop-2-en-1-yl)-1H-imidazol-5-yl]-1H-indole;
4-bromo-3-(1-ethyl-1H-imidazol-5-yl)-1H-indole;
3-(1-ethyl-1H-imidazol-5-yl)-5-fluoro-1H-indole;
5-chloro-3-(1-ethyl-1H-imidazol-5-yl)-1H-indole;
5-bromo-3-(1-ethyl-1H-imidazol-5-yl)-1H-indole;
5-iodo-3-(1-ethyl-1H-imidazol-5-yl)-1H-indole;
3-(1-ethyl-1H-imidazol-5-yl)-1H-indole-5-carbonitrile;
3-(1-ethyl-1H-imidazol-5-yl)-5-methyl-1H-indole;
3-(1-ethyl-1H-imidazol-5-yl)-1H-indol-5-ol;
3-(1-ethyl-1H-imidazol-5-yl)-4-methoxy-1H-indole;
3-(1-ethyl-1H-imidazol-5-yl)-7-methyl-1H-indole;
3-(1-ethyl-1H-imidazol-5-yl)-1H-indole;
5-methoxy-3-[1-(3-methoxypropyl)-1H-imidazol-5-yl]-1H-indole;
5-benzyloxy-3-(1-ethyl-1H-imidazol-5-yl)-1H-indole;
3-(1-ethyl-1H-imidazol-5-yl)-7-fluoro-5-iodo-1H-indole;
3-(1-ethyl-1H-imidazol-5-yl)-1H-indole-5-carboxamide;
3-(1-cyclopropyl-1H-imidazol-5-yl)-5-iodo-1H-indole;
5-methoxy-3-[1-(2-phenylethyl)-1H-imidazol-5-yl]-1H-indole;
5-(1-ethyl-1H-imidazol-5-yl)-1H-indole;
6-(1-ethyl-1H-imidazol-5-yl)-1H-indole;
3-(1H-imidazol-5-yl)-1H-indole;
or a pharmaceutically acceptable salt thereof.

The most preferred compounds according to the invention are as follows:
5-methoxy-3-(1-methyl-1H-imidazol-5-yl)-1H-indole;
3-(1-ethyl-1H-imidazol-5-yl)-5-methoxy-1H-indole;
5-methoxy-3-(1-propyl-1H-imidazol-5-yl)-1H-indole;
5-chloro-3-(1-ethyl-1H-imidazol-5-yl)-1H-indole;
5-bromo-3-(1-ethyl-1H-imidazol-5-yl)-1H-indole;
3-(1-ethyl-1H-imidazol-5-yl)-5-iodo-1H-indole;
3-(1-ethyl-1H-imidazol-5-yl)-5-methyl-1H-indole;
3-(1-ethyl-1H-imidazol-5-yl)-1H-indol-5-ol;
3-(1-ethyl-1H-imidazol-5-yl)-7-fluoro-5-iodo-1H-indole;
3-(1-ethyl-1H-imidazol-5-yl)-1H-indole-5-carboxamide;
or a pharmaceutically acceptable salt thereof.

Further most preferred compounds according to the invention are as follows:
4-fluoro-5-iodo-3-(1-methyl-1H-imidazol-5-yl)-1H-indole;
3-(1-ethyl-1H-imidazol-5-yl)-4-fluoro-5-iodo-1H-indole;
5-bromo-3-(1-ethyl-1H-imidazol-5-yl)-4-fluoro-1H-indole;
3-(1-ethyl-1H-imidazol-5-yl)-4-fluoro-1H-indole-5-carboxamide;
4-fluoro-3-(1-methyl-1H-imidazol-5-yl)-1H-indole-5-carboxamide;
4-fluoro-3-(1-ethyl-1H-imidazol-5-yl)-1H-indole;
or a pharmaceutically acceptable salt thereof.

In another aspect, the invention concerns a compound as defined above, for use in the treatment or prevention of a disease or disorder selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders.

Since many chemical elements can occur as isotopes, their abundance in the molecule of the inventive compound of Formula (I) may be identical as in the nature or altered. Some isotopes exhibit different spectral or biological properties, and this phenomenon may be used for analysis of distribution and metabolism of drugs in the body of the recipient. All forms of the compounds of Formula (I), both having a natural or unnatural abundance of isotopes of any of their constituent elements are intended to be within the scope of this invention.

In the preferred embodiment, the invention concerns a compound as defined above, being isotopically labelled for use in the in vitro and in vivo diagnostics or imaging of 5-HT$_7$ serotonin receptor.

Examples of isotopes that can be incorporated into the intermediates or compounds of the invention include isotopes of hydrogen, carbon, nitrogen, oxygen, fluorine and iodine, such as $^3$H, $^{11}$C, $^{14}$C, $^{13}$N, $^{15}$O, $^{18}$F, $^{125}$I, and $^{131}$I.

The synthetic procedure 4 below illustrates preparation of isotopically labelled compounds of the invention in more detail.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) *Harrison's Principles of Internal Medicine,* 13 ed., 1814-1882, being incorporated herein in its entirety by reference). Thus, in one aspect, the invention concerns a pharmaceutical composition comprising a therapeutically effective amount of one or more compounds according to the invention as an active component, and one or more pharmaceutical excipients, for use in the treatment or prevention of a disease or disorder selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders.

The exact nature of the excipient, or, for example carrier or diluent, will depend upon the desired use for the composition, and may be suitable or acceptable for veterinary use and/or suitable or acceptable for human use. A detailed teaching on the principles of selecting the excipients for pharmaceutical compositions to be administered in various ways is presented in A. R. Gennaro, *Remington: The Science and Practice of Pharmacy*, Lippincott, Williams and Wilkins, 2000, being incorporated herein in its entirety by reference.

Therefore, the invention concerns the pharmaceutical composition as defined above, to be administered orally, parenterally, by inhalation, transdermally, or transmucosally.

The composition may optionally include one or more additional compounds, including one or more additional therapeutic agents.

In particular embodiment, the invention concerns the pharmaceutical composition as defined above, that comprises additional 5-HT$_7$-active components selected from the group comprising aripiprazole, amisulpride, chlorpromazine, clozapine, risperidone, ziprasidone, fluoxetine, 5-CT, 5-methoxytryptamine, 8-OH-DPAT, aripiprazole, AS-19, E-55888, MSD-5a, LP-12, LP-44, LP-211, RA-7, and N$^\omega$-methylserotonin.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

The invention discloses also a method of treating a disease or disorder in a mammal, wherein the disease or disorder is selected from Rett syndrome, Fragile X syndrome, mood disorders including depression, anxiety, sleep disorders, gut disorders, pain, schizophrenia, inflammatory processes in the CNS, dementia, Alzheimer's disease, autistic disorder and other neuropsychiatric disorders, the method comprising administering to said mammal a therapeutically effective amount of a compound according to the invention.

The inventors unexpectedly found that the compounds of Formula (I) are potent and selective agonists of the 5-HT$_7$ serotonin receptor.

These compounds were tested against an array of receptors using the radioligand displacement methodology. The experimental details of the assays are summarised in Table 1 and Table 2. Within the synthesized library of compounds, the compounds that exhibited the highest affinity for 5-HT$_7$ serotonin receptor were selected for functional assay to determine their efficacy as agonists. The results are summarized in Table 3. All examples showed excellent selectivity over 5-HT$_6$ and 5-HT$_{7A}$ receptors ($K_i$>1000 nM).

Two compounds, examples 4 and 14 were selected for additional CNS-target screening (at two concentrations, $10^{-6}$ and $10^{-8}$ M) in order to check their selectivity over $\alpha_1$, $\alpha_2$c, CB$_1$, D$_3$, H$_1$, 5-HT$_{1B}$, 5-HT$_{2B}$, 5-HT$_{5A}$ receptors. The results are summarized in Table 4.

Halogens, especially fluorine and chlorine, are widely used substituents in medicinal chemistry. Until recently, they were merely perceived as hydrophobic moieties and Lewis bases in accordance with their electronegativities. Much in contrast to this perception, compounds containing chlorine, bromine, or iodine can also form directed close contacts of the type R—X . . . Y—R', where the halogen X acts as a Lewis acid and Y can be any electron donor moiety. This interaction, referred to as "halogen bonding" is driven by the σ-hole, a positively charged region on the hind side of X along the R—X bond axis that is caused by an anisotropy of electron density on the halogen.[32,33,34] Virtual docking of the described compounds to homology models of 5-HT$_7$ receptor using hybrid quantum mechanics/molecular mechanics protocol indicated involvement of halogen bonding in binding of compounds from Examples 12-14, 25, and 27. Theoretically, electron withdrawing substituents on an aromatic system substituted with a halogen can reinforce the halogen bonding. This finding has been proven experimentally and implicates that the compounds of the invention, where R5=halogen and at least one of the substituents R4, R6, R7 is an electron withdrawing group, could possess enhanced 5-HT$_7$ receptor activity.

General Synthetic Procedures

The compounds of Formula (I) can be prepared according to any relevant procedure available to the person skilled in the art of chemical synthesis. Just to assist in developing the synthetic pathway, several examples are described herein in detail. There is much freedom in the choice of the reaction conditions, owing to click-chemistry properties of Van Leusen imidazole synthesis.

Scheme 1 depicts the method employed in the synthesis of the compounds of Formula (I), where R3 is the substituted imidazolyl. Here, an appropriately substituted indole-3-carbaldehyde reacts with an appropriate amine, then the obtained imine reacts with TOSMIC. The formed intermediate eliminates tosyl group, thus aromatizing the imidazole system to afford a compound of Formula (I). See the general procedure 1 below.

Scheme 1

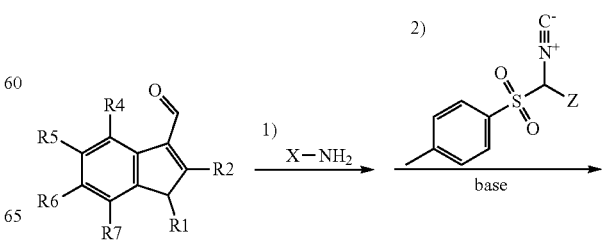

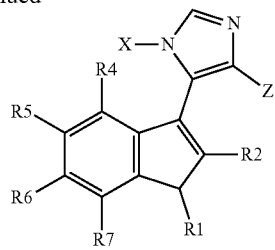

The substrate for this reaction, bearing 3-carbaldehyde group, can be prepared via the general procedure 2, as described below. The indole nitrogen of such a compound can be substituted with R1 substituent via the general procedure 3, as described below. The compounds according to the invention can be radiolabelled at any convenient stage of their synthesis. An example of such radiolabelling is described in the general procedure 4 and depicted in Scheme 2 below.

General Procedure 1 for the Synthesis of Compounds of Formula (I)

An aromatic aldehyde (3 mmol) was mixed with an amine (15 mmol) in 20 ml of dry methanol. The reaction mixture was left overnight to complete imine formation although it could be TLC monitored ($SiO_2$/$CHCl_3$). Anhydrous $K_2CO_3$ (3 mmol) and TOSMIC (tosylmethyl isocyanide, 3 mmol) were subsequently added. The mixture was stirred for additional 8 hours, diluted with 50 ml of $H_2O$, and extracted three times with 20 ml of ethyl acetate. The combined extracts were washed twice with 20 ml of $H_2O$, and once with 20 ml of brine, treated with anhydrous magnesium sulphate and evaporated. The final products were purified either by trituration under 2:1 hexane:isopropanol mixture, or chromatographed on a short silica gel bed. The unreacted aldehydes were eluted with ethyl acetate or chloroform, and then a mixture of AcOEt:MeOH or $CHCl_3$:MeOH was applied to elute the product.

General Procedure 2 for the Synthesis of Substituted Indole-3-Carbaldehydes

The Vilsmeier-Haack reagent was generated by the addition of 2 ml of $POCl_3$ over the course of 15 minutes to 8 ml of DMF cooled in an ice-salt bath. After the addition was complete, the ice bath was removed and the contents of the flask allowed to warm to room temperature over approx. 30 minutes. The substituted indole (21.9 mmol) was dissolved in 10 ml of DMF and added over a period of 15 minutes to the formylating mixture. The stirring was continued for an hour during which the flask contents were heated to 40° C. in a hot water bath. A total of 50 ml ice cold $H_2O$ and 20 ml of 5 M NaOH were added, the mixture quickly brought to a boil and left to cool slowly. The crystals were removed by filtration, washed with cold water and vacuum dried. The products thus obtained were in most cases sufficiently pure for the subsequent reactions, and the impure aldehydes were recrystallized from ethanol-water mixtures. Yields varied from 48 to 90%.

General Procedure 3 for the Synthesis of 1-Alkyl Substituted 3-Carbaldehydes

A total of 10 mmol of an appropriate indole-carbaldehyde, 50 ml of toluene, 36 ml of 30% NaOH solution, 1 mmol (322 mg) of tetrabutylammonium bromide (TBAB) and 10.5 mmol of alkyl iodide (0.66 ml of methyl iodide, for instance) were placed in a stoppered flask. The mixture was stirred until the substrate disappeared on TLC (on average 12 h). After completion of the reaction, the phases were separated, next the organic extract was washed with 30 ml of $H_2O$ followed by 30 ml brine, and was dried over $MgSO_4$, and toluene was rotary evaporated. Sodium metabisulfite (40 mmol) dissolved in 13 ml water and 15 ml ethanol were added to the obtained oil. The formed adduct was vacuum filtered, washed sparingly with cold ethanol and transferred to a vigorously stirred 10% NaOH solution (50 ml). The precipitated product was extracted with three 25 ml portions of ethyl acetate, the extracts were washed with 25 ml water, followed with 25 ml brine, dried over $MgSO_4$, and the solvent was rotary evaporated. The crude product was triturated twice with 5 ml of hexane:isopropanol 2:1 mixture, vacuum filtered, and dried.

General Procedure 4 for Radiosynthesis

The incorporation of $^{11}C$ atoms into the compounds of Formula (I) may be achieved, for example, by reaction of a suitable precursor bearing a phenolic hydroxyl group and, if needed, a protecting group such as tert-butoxycarbonyl (Boc), with a radioactive alkylating agent such as $[^{11}C]CH_3I$, $[^{11}C]CH_3CH_2I$, $[^{11}C]CH_3OTf$, or $[_{11}C]CH_3Ch_2OTf$. The reaction is performed in an inert solvent such as dimethylformamide, in the presence of a strong base such as NaOH, by stirring the reaction mixture at a suitable temperature until completion of the reaction. In the case of the protected substrate, the protecting group is then removed; in the case of Boc group, treatment with a strong acid such as hydrochloric or trifluoroacetic acid is required.

Scheme 2 depicts an exemplary synthetic path towards the $^{11}C$ radioligand. All the shown reactions were performed on non-radioactive ("cold") chemicals using LC-MS to monitor the purity of the obtained intermediates. NMR and MS spectra of 3-(1-ethyl-1H-imidazol-5-yl)-5-methoxy-1H-indole prepared by this reaction sequence are identical to the spectra of the product of Example 4 being prepared via the general procedure 1.

Scheme 2

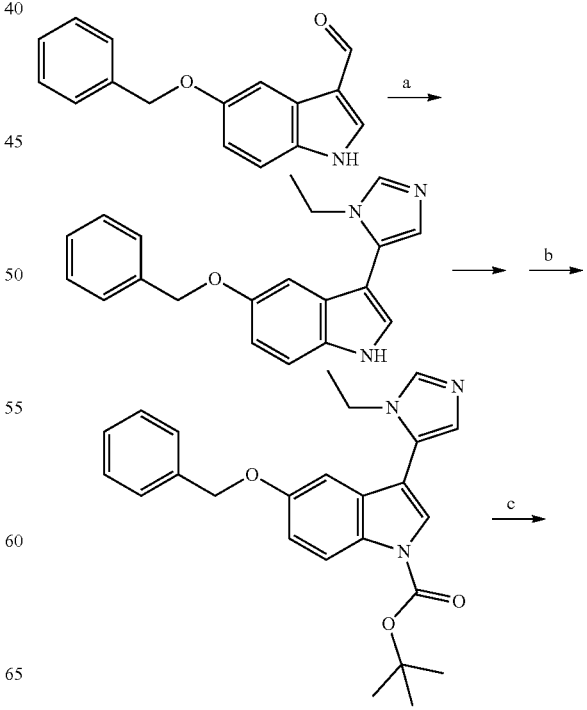

-continued

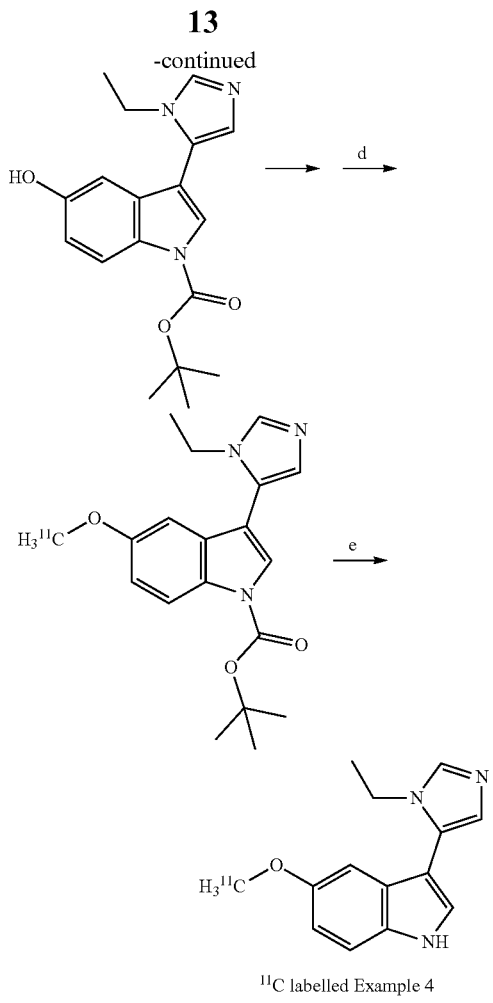

$^{11}$C labelled Example 4

Reaction conditions: a) EtNH$_2$, TOSMIC, K$_2$CO$_3$, MeOH (according to the general procedure 1); b) Boc$_2$O, DMAP, THF; c) Pd/C, H$_2$, MeOH; d) $^{11}$CH$_3$I, NaOH, toluene, H$_2$O, TBAB; e) HCl, MeOH.

Experimental Procedure

Abbreviations

AcOEt ethyl acetate
Boc tert-butoxycarbonyl
CNS central nervous system
DMAP p-dimethylaminopyridine
DMF N,N-dimethylformamide
DMSO dimethyl sulphoxide
DMSO-d$_6$ perdeuterated dimethyl sulphoxide
EDTA ethylenediaminetetraacetic acid
ESI+ electrospray ionisation in positive mode
LC-MS liquid chromatography followed by mass spectroscopy
MPO multi parameter optimization
PBS phosphate buffered saline
ppm parts per million
TBAB tetrabutylammonium bromide
TLC thin layer chromatography
TPSA topological polar surface area
TMS tetramethylsilane
TOSMIC p-toluenesulphonyl isocyanate
tosyl p-toluenesulphonyl Chemical Synthesis All organic reagents were purchased from Sigma-Aldrich, Apollo Scientific Apollo Scientific Ltd, or Combi-Blocks and were used without purification. Solvents and inorganic reagents were acquired from Chempur. Reaction progress was monitored by TLC on Merck Silica Gel 60 F$_{254}$ on aluminium plates. Column chromatography was performed on Merck Silica Gel 60 (0.063-0.200 mm; 70-230 mesh ASTM). UPLC/MS analysis was performed on Waters TQD spectrometer combined with UPLC Acquity H-Class with PDA eLambda detector. Waters Acquity UPLC BEH C18 1.7 µm 2.1×100 mm chromatographic column was used, at 40° C., 0.300 ml/min flow rate and 1.0 µL injection volume (the samples were dissolved in LC-MS grade acetonitrile, typically at a concentration of 0.1-1 mg/ml prior to injection). All mass spectra were recorded under electrospray ionization in positive mode (ESI+) and chromatograms were recorded with UV detection in the range of 190-300 nm. The gradient conditions used were: 80% phase A (water+0.1% formic acid) and 20% phase B (acetonitrile+0.1% formic acid) to 100% phase B (acetonitrile+0.1% formic acid) at 3.0 minutes, kept till 3.5 minutes, then to initial conditions until 4.0 minutes and kept for additional 2.0 minutes. Total time of analysis—6.0 minutes.

$^1$H and $^{13}$C NMR spectra were recorded on a Bruker Avance III HD 400 NMR spectrometer. All samples were dissolved in DMSO-d$_6$ with TMS as the internal standard. The spectral data of new compounds refer to their free bases.

Example 1.
3-(1-methyl-1H-imidazol-5-yl)-1H-indole

The compound was synthesized from indole-3-carbaldehyde (3 mmol) and methylamine according to the general procedure 1 and purified via column chromatography (SiO$_2$, CHCl$_3$, then 19:1 CHCl$_3$:MeOH) (91% yield).

LC-MS: m/z=198.17; t$_R$=0.77 min. $^1$H NMR (500 MHz, DMSO-d$_6$, TMS, ppm) δ=11.48 (s, 1H), 7.74 (d, J=1.1 Hz, 1H), 7.65-7.55 (m, 2H), 7.46 (dt, J=8.1, 0.9 Hz, 1H), 7.21-7.03 (m, 3H), 3.66 (s, 3H).

$^{13}$C NMR (126 MHz, DMSO-d$_6$, TMS, ppm) δ=32.09, 103.74, 111.77, 119.01, 119.58, 121.69, 123.96, 126.06, 126.15, 126.86, 136.03, 138.09.

Example 2. 5-methoxy-3-(1-methyl-1H-imidazol-5-yl)-1H-indole

The compound was synthesized from 5-methoxyindole-3-carbaldehyde (3 mmol) and methylamine according to the general procedure 1 and purified by trituration with 2:1 hexane:isopropyl alcohol mixture (55% yield).

LC-MS: m/z=228.1; t$_R$=0.74 min. $^1$H NMR (500 MHz, DMSO-d$_6$, TMS, ppm) δ=11.34-11.29 (m, 1H), 7.72-7.66 (m, 1H), 7.54 (d, J=2.6 Hz, 1H), 7.35 (dd, J=8.8, 0.6 Hz, 1H), 7.09 (d, J=1.2 Hz, 1H), 7.01 (d, J=2.5 Hz, 1H), 6.81 (dd, J=8.8, 2.4 Hz, 1H), 3.76 (s, 3H), 3.65 (d, J=0.5 Hz, 3H).
$^{13}$C NMR (126 MHz, DMSO-d$_6$, TMS, ppm) δ=31.96, 39.00, 55.26, 100.40, 103.66, 112.03, 112.51, 119.49, 124.51, 126.38, 126.50, 126.89, 131.07, 138.08, 153.90.

Example 3. 3-(1-ethyl-1H-imidazol-5-yl)-1-methyl-1H-indole

The compound was synthesized from 1-methylindole-3-carbaldehyde (3 mmol) and ethylamine according to the general procedure 1 and purified via column chromatography (SiO$_2$, AcOEt, then 49:1 AcOEt:MeOH) (82% yield).

LC-MS: m/z=226.1; t$_R$=0.42 min. $^1$H NMR (500 MHz, DMSO-d$_6$, TMS, ppm) δ=7.78 (d, J=1.2 Hz, 1H), 7.56-7.45 (m, 3H), 7.23 (ddd, J=8.2, 7.0, 1.2 Hz, 1H), 7.11 (ddd, J=8.0, 7.0, 1.0 Hz, 1H), 7.02 (d, J=1.2 Hz, 1H), 4.00 (q, J=7.2 Hz, 2H), 3.85 (s, 3H), 1.23 (t, J=7.3 Hz, 3H). $^{13}$C NMR (126 MHz, DMSO-$d_6$, TMS, ppm) δ=16.30, 32.57, 39.02, 56.13, 89.44, 103.02, 110.07, 119.10, 119.74, 121.78, 125.39, 126.78, 127.21, 128.17, 136.50, 137.06.

Example 4. 3-(1-ethyl-1H-imidazol-5-yl)-5-methoxy-1H-indole

The compound was synthesized from 5-methoxyindole-3-carbaldehyde (3 mmol) and ethylamine according to the general procedure 1 and purified via column chromatography (SiO$_2$, AcOEt, then 19:1 AcOEt:MeOH) and additional trituration with hexane:acetone 9:1 (49% yield).

LC-MS: m/z=242.16; $t_R$=0.5-1.01 min. $^1$H NMR (500 MHz, DMSO-$d_6$, TMS, ppm) δ=11.30 (s, 1H), 7.77 (d, J=1.1 Hz, 1H), 7.47 (d, J=2.6 Hz, 1H), 7.35 (dd, J=8.8, 0.6 Hz, 1H), 7.02 (d, J=1.1 Hz, 1H), 6.93 (d, J=2.4 Hz, 1H), 6.80 (dd, J=8.7, 2.4 Hz, 1H), 4.00 (q, J=7.3 Hz, 2H), 3.74 (s, 3H), 1.23 (t, J=7.2 Hz, 3H). $^{13}$C NMR (126 MHz, DMSO-$d_6$, TMS, ppm) δ=153.87, 136.88, 131.05, 127.02, 126.85, 125.86, 124.71, 112.55, 112.02, 103.59, 100.14, 55.23, 39.42, 16.24.

Example 5. 3-(1-propyl-1H-imidazol-5-yl)-5-methoxy-1H-indole

The compound was synthesized from 5-methoxyindole-3-carbaldehyde (3 mmol) and propylamine according to the general procedure 1 and purified via column chromatography (SiO$_2$, AcOEt, then 49:1 AcOEt:MeOH) (77% yield).

LC-MS: m/z=256.22; $t_R$=1.44 min. $^1$H NMR (500 MHz, DMSO-$d_6$, TMS, ppm) δ=11.30-11.26 (m, 1H), 7.74 (d, J=1.1 Hz, 1H), 7.46 (d, J=2.6 Hz, 1H), 7.35 (dd, J=8.7, 0.6 Hz, 1H), 7.01 (d, J=1.1 Hz, 1H), 6.91 (d, J=2.4 Hz, 1H), 6.80 (dd, J=8.8, 2.5 Hz, 1H), 3.97-3.90 (m, 2H), 3.74 (s, 3H), 1.63-1.52 (m, 2H), 0.74 (t, J=7.4 Hz, 3H). $^{13}$C NMR (126 MHz, DMSO-$d_6$, TMS, ppm) δ=172.06, 153.87, 137.59, 131.05, 127.09, 126.92, 124.70, 112.55, 111.99, 103.67, 100.14, 55.23, 46.06, 23.51, 10.83.

Example 6. 3-(1-butyl-1H-imidazol-5-yl)-5-methoxy-1H-indole

The compound was synthesized from 5-methoxyindole-3-carbaldehyde (3 mmol) and butylamine according to the general procedure 1 and purified via column chromatography (SiO$_2$, CHCl$_3$, then 19:1 CHCl$_3$:MeOH) (40% yield).

LC-MS: m/z=270.15; $t_R$=1.76 min. $^1$H NMR (500 MHz, DMSO-$d_6$, TMS, ppm) δ=11.30-11.25 (m, 1H), 7.77-7.71 (m, 1H), 7.46 (d, J=2.6 Hz, 1H), 7.34 (dd, J=8.8, 0.6 Hz, 1H), 7.01 (s, 1H), 6.91 (d, J=2.4 Hz, 1H), 6.80 (dd, J=8.8, 2.4 Hz, 1H), 3.97 (t, J=7.3 Hz, 2H), 3.74 (s, 3H), 1.54 (p, 2H), 1.15 (h, 2H), 0.75 (t, J=7.4 Hz, 3H). $^{13}$C NMR (126 MHz, DMSO-$d_6$, TMS, ppm) δ=13.31, 19.12, 21.06, 32.23, 39.00, 44.15, 54.66, 55.22, 100.12, 103.63, 111.99, 112.17, 112.54, 124.74, 126.01, 126.91, 126.92, 127.01, 128.90, 131.03, 131.04, 137.53, 153.86, 172.01.

Example 7. 3-(1-cyclopropyl-1H-imidazol-5-yl)-5-methoxy-1H-indole

The compound was synthesized from 5-methoxyindole-3-carbaldehyde (3 mmol) and cyclopropylamine according to the general procedure 1 and purified via column chromatography (SiO$_2$, CHCl$_3$, then 19:1 CHCl$_3$:MeOH) (40% yield).

LC-MS: m/z=254.09; $t_R$=0.98 min. $^1$H NMR (500 MHz, DMSO-$d_6$, TMS, ppm) δ=11.29-11.25 (m, 1H), 7.71-7.65 (m, 2H), 7.35 (dd, J=8.7, 0.5 Hz, 1H), 7.11 (dd, J=19.9, 1.8 Hz, 2H), 6.81 (dd, J=8.7, 2.4 Hz, 1H), 3.77 (s, 3H), 3.46 (tt, J=7.0, 4.1 Hz, 1H), 0.99-0.87 (m, 4H). $^{13}$C NMR (126 MHz, DMSO-$d_6$, TMS, ppm) δ=153.84, 136.95, 130.96, 128.21, 126.19, 126.06, 124.29, 112.44, 111.91, 104.08, 100.63, 55.26, 27.14, 25.49, 6.99.

Example 8. 5-methoxy-3-[1-(prop-2-en-1-yl)-1H-imidazol-5-yl]-1H-indole

The compound was synthesized from 5-methoxyindole-3-carbaldehyde (3 mmol) and allylamine according to the general procedure 1 and purified via crystallisation (AcOEt) and trituration with hexane:isopropanol 2:1 mixture (3% yield).

LC-MS: m/z=254.09; $t_R$=0.49-1.22 min. $^1$H NMR (500 MHz, DMSO-$d_6$, TMS, ppm) δ=11.24 (s, 1H), 7.69 (d, J=1.1 Hz, 1H), 7.41 (d, J=2.7 Hz, 1H), 7.33 (dd, J=8.7, 0.5 Hz, 1H), 7.08 (d, J=1.1 Hz, 1H), 6.95 (d, J=2.4 Hz, 1H), 6.79 (dd, J=8.7, 2.4 Hz, 1H), 5.97 (ddt, J=17.1, 10.2, 5.0 Hz, 1H), 5.13 (dq, J=10.4, 1.6 Hz, 1H), 4.89 (dq, J=17.1, 1.7 Hz, 1H), 4.63 (dt, J=5.0, 1.8 Hz, 2H), 3.74 (s, 3H). $^{13}$C NMR (126 MHz, DMSO-$d_6$, TMS, ppm) δ=39.03, 40.03, 46.60, 55.26, 100.23, 103.37, 112.04, 112.53, 116.50, 124.51, 126.31, 126.73, 126.81, 131.02, 134.86, 137.61, 153.88.

Example 9. 6-bromo-3-(1-ethyl-1H-imidazol-5-yl)-1H-indole

The compound was synthesized from 6-bromoindole-3-carbaldehyde (3 mmol) and ethylamine according to the general procedure 1 and purified via column chromatography (SiO$_2$, AcOEt, then 19:1 CHCl$_3$:MeOH) (70% yield).

LC-MS: m/z=289.95 and 291.88 (for both bromine isotopes); $t_R$=1.82 min. $^1$H NMR (500 MHz, DMSO-$d_6$, TMS, ppm) δ 11.57 (s, 1H), 7.77 (d, J=1.1 Hz, 1H), 7.64 (dd, J=1.8, 0.5 Hz, 1H), 7.57 (d, J=2.5 Hz, 1H), 7.45 (d, J=8.5, 0.6 Hz, 1H), 7.19 (dd, J=8.5, 1.8 Hz, 1H), 7.01 (d, J=1.1 Hz, 1H), 3.99 (q, J=7.2 Hz, 2H), 1.20 (t, 3H). $^{13}$C NMR (126 MHz, DMSO, TMS, ppm) δ 137.21, 136.88, 127.41, 125.52, 125.10, 125.02, 122.46, 120.68, 114.38, 114.32, 104.18, 40.02, 39.49, 16.18.

Example 10. 4-bromo-3-(1-ethyl-1H-imidazol-5-yl)-1H-indole

The compound was synthesized from 4-bromoindole-3-carbaldehyde (3 mmol) and ethylamine according to the general procedure 1 and purified via column chromatography (SiO$_2$, AcOEt, then 19:1 CHCl$_3$:MeOH) and additional trituration with hexane:isopropanol 2:1 mixture (9% yield).

LC-MS: m/z=289.95 and 291.88 (for both bromine isotopes); $t_R$=1.84 min. 1H NMR (500 MHz, DMSO-$d_6$, TMS, ppm) δ 11.78 (s, 1H), 7.76 (d, J=1.2 Hz, 1H), 7.59-7.45 (m, 2H), 7.22 (dd, J=7.6, 0.8 Hz, 1H), 7.05 (t, 1H), 6.83 (s, 1H), 3.72 (q, J=7.3 Hz, 2H), 1.13 (t, J=7.3 Hz, 3H). 13C NMR (126 MHz, DMSO, TMS, ppm) δ 137.19, 136.44, 129.72, 128.64, 125.47, 124.40, 123.46, 122.69, 112.48, 111.73, 103.29, 15.95.

Example 11. 3-(1-ethyl-1H-imidazol-5-yl)-5-fluoro-1H-indole

The compound was synthesized from 5-fluoroindole-3-carbaldehyde (3 mmol) and ethylamine according to the general procedure 1 and purified via trituration with hexane: isopropanol 2:1 mixture (24% yield).

LC-MS: m/z=230.10; $t_R$=1.47 min. $^1$H NMR (500 MHz, DMSO-d$_6$, TMS, ppm) δ 11.56 (s, 1H), 7.77 (s, 1H), 7.62 (d, J=2.6 Hz, 1H), 7.46 (ddd, J=8.8, 4.7, 0.6 Hz, 1H), 7.23-7.17 (m, 1H), 7.05-6.97 (m, 2H), 4.00 (q, J=7.2 Hz, 2H), 1.22 (t, J=7.3 Hz, 3H). $^{13}$C NMR (126 MHz, DMSO-d$_6$, TMS, ppm) δ 158.30, 156.46, 137.11, 132.69, 127.22, 126.78, 126.17, 125.22, 112.94, 110.05, 104.14, 103.57, 16.19.

Example 12. 5-chloro-3-(1-ethyl-1H-imidazol-5-yl)-1H-indole

The compound was synthesized from 5-chloroindole-3-carbaldehyde (3 mmol) and ethylamine according to the general procedure 1 and purified via trituration with hexane: isopropanol 2:1 mixture (50% yield).

LC-MS: m/z=246.09; $t_R$=1.75 min. $^1$H NMR (500 MHz, DMSO-d$_6$, TMS, ppm) δ=11.67 (s, 1H), 7.78 (d, J=1.1 Hz, 1H), 7.63 (s, 1H), 7.53-7.41 (m, 2H), 7.16 (dd, J=8.6, 2.1 Hz, 1H), 7.03 (d, J=1.1 Hz, 1H), 4.00 (p, J=7.3 Hz, 2H), 1.27-1.11 (m, 3H). $^{13}$C NMR (126 MHz, DMSO-d$_6$, TMS, ppm) δ=14.06, 16.19, 20.73, 38.99, 59.73, 103.65, 103.66, 113.41, 117.88, 121.71, 124.30, 124.90, 125.98, 127.45, 127.66, 134.48, 137.21.

Example 13. 5-bromo-3-(1-ethyl-1H-imidazol-5-yl)-1H-indole

The compound was synthesized from 5-bromoindole-3-carbaldehyde (3 mmol) and ethylamine according to the general procedure 1 and purified via trituration with hexane: isopropanol 2:1 mixture (45% yield).

LC-MS: m/z=289.95 and 291.88 (for both bromine isotopes); $t_R$=1.87 min. $^1$H NMR (500 MHz, DMSO-d$_6$, TMS, ppm) δ 11.78 (s, 1H), 7.76 (d, J=1.2 Hz, 1H), 7.59-7.45 (m, 2H), 7.22 (dd, J=7.6, 0.8 Hz, 1H), 7.10-7.02 (m, 1H), 6.83 (d, J=1.1 Hz, 1H), 3.72 (q, J=7.3 Hz, 2H), 1.13 (t, J=7.3 Hz, 3H). $^{13}$C NMR (126 MHz, DMSO, TMS, ppm) δ 137.24, 134.71, 128.38, 127.50, 125.84, 124.85, 124.24, 120.90, 113.88, 112.22, 103.54, 39.46, 16.21.

Example 14. 5-iodo-3-(1-ethyl-1H-imidazol-5-yl)-1H-indole

The compound was synthesized from 5-iodoindole-3-carbaldehyde (3 mmol) and ethylamine according to the general procedure 1 and purified via trituration with hexane: isopropanol 2:1 mixture (42% yield).

LC-MS: m/z=337.81; $t_R$=2.16 min. $^1$H NMR (500 MHz, DMSO-d$_6$, TMS, ppm) δ=11.64 (s, 1H), 7.81-7.75 (m, 2H), 7.56 (d, J=2.2 Hz, 1H), 7.42 (dd, J=8.5, 1.7 Hz, 1H), 7.33 (dd, J=8.5, 0.5 Hz, 1H), 7.00 (d, J=1.1 Hz, 1H), 3.98 (q, J=7.3 Hz, 2H), 1.20 (t, J=7.2 Hz, 3H). $^{13}$C NMR (126 MHz, DMSO-d$_6$, TMS, ppm) δ=16.23, 79.17, 83.40, 83.42, 83.42, 103.14, 103.15, 114.32, 119.50, 124.88, 125.35, 127.07, 127.53, 129.26, 129.26, 129.67, 135.06, 137.23.

Example 15. 3-(1-ethyl-1H-imidazol-5-yl)-1H-indole-5-carbonitrile

The compound was synthesized from 5-cyanoindole-3-carbaldehyde (3 mmol) and ethylamine according to the general procedure 1 and purified via trituration with hexane: isopropanol 2:1 mixture (60% yield).

LC-MS: m/z=237.10; $t_R$=0.82 min. $^1$H NMR (500 MHz, DMSO-d$_6$, TMS, ppm) δ=12.03 (s, 1H), 7.99 (dd, J=1.6, 0.7 Hz, 1H), 7.83-7.75 (m, 2H), 7.63 (dd, J=8.4, 0.7 Hz, 1H), 7.51 (dd, J=8.5, 1.6 Hz, 1H), 7.12 (d, J=1.1 Hz, 1H), 4.02 (q, J=7.3 Hz, 2H), 1.21 (t, J=7.2 Hz, 3H). $^{13}$C NMR (126 MHz, DMSO-d$_6$, TMS, ppm) δ=137.76, 137.51, 127.86, 126.62, 126.24, 124.55, 124.51, 124.32, 120.48, 113.16, 105.00, 101.83, 39.57, 16.12.

Example 16. 3-(1-ethyl-1H-imidazol-5-yl)-5-methyl-1H-indole

The compound was synthesized from 5-methylindole-3-carbaldehyde (3 mmol) and ethylamine according to the general procedure 1 and purified via trituration with hexane: isopropanol 2:1 mixture (51% yield).

LC-MS: m/z=225.97; $t_R$=1.61 min. $^1$H NMR (500 MHz, DMSO-d$_6$, TMS, ppm) δ=11.31-11.27 (m, 1H), 7.75 (d, J=1.1 Hz, 1H), 7.46 (d, J=2.6 Hz, 1H), 7.33 (dd, J=8.2, 0.8 Hz, 1H), 7.27 (dq, J=1.6, 0.8 Hz, 1H), 7.02-6.94 (m, 2H), 3.99 (q, J=7.2 Hz, 2H), 2.37 (t, J=0.6 Hz, 3H), 1.21 (t, J=7.2 Hz, 3H). $^{13}$C NMR (126 MHz, DMSO-d$_6$, TMS, ppm) δ=16.25, 21.23, 103.27, 111.47, 118.39, 119.50, 123.25, 124.15, 125.82, 126.76, 127.16, 128.11, 134.36, 136.87.

Example 17. 3-(1-ethyl-1H-imidazol-5-yl)-1H-indol-5-ol

The compound was synthesized by hydrogenation of Example 24 over palladium on carbon. The substrate was dissolved in methanol in a pressure reactor, 10 mol % Pd/C was added. The reactor was sealed and pressurized to 7 bar with H$_2$. Completion of the reaction was monitored with LC-MS. The mixture was then filtered through Celite which was then washed with MeOH. Solvent was stripped off on a rotary evaporator and the resulting solid was triturated under hexane:isopropanol:acetone 3:1:1 mixture. Yield: 65%.

LC-MS: m/z=228.16; $t_R$=0.45 min. $^1$H NMR (500 MHz, DMSO-d$_6$, TMS, ppm) δ 11.13 (s, 1H), 8.82 (s, 1H), 7.75 (s, 1H), 7.40 (d, J=2.6 Hz, 1H), 7.24 (d, J=8.6 Hz, 1H), 6.93 (s, 1H), 6.80 (d, J=2.3 Hz, 1H), 6.67 (dd, J=8.6, 2.3 Hz, 1H), 3.98 (q, J=7.3 Hz, 2H), 1.22 (t, J=7.2 Hz, 3H). $^{13}$C NMR (126 MHz, DMSO-d$_6$, TMS, ppm) δ 151.26, 130.43, 127.31, 126.77, 124.47, 112.19, 112.01, 102.86, 102.55, 73.71, 39.40, 25.49, 16.27.

Example 18. 3-(1-benzyl-1H-imidazol-5-yl)-5-methoxy-1H-indole

The compound was synthesized from 5-methoxyindole-3-carbaldehyde (3 mmol) and benzylamine according to the general procedure 1 and purified via column chromatography (SiO$_2$, AcOEt) (37% yield).

LC-MS: m/z=304.15; $t_R$=1.86 min. $^1$H NMR (500 MHz, DMSO-d$_6$, TMS, ppm) δ=11.21 (s, 1H), 7.83 (d, J=1.2 Hz, 1H), 7.36-7.18 (m, 6H), 7.14 (d, J=1.2 Hz, 1H), 6.99 (ddt, J=7.5, 1.3, 0.7 Hz, 2H), 6.93 (d, J=2.4 Hz, 1H), 6.78 (dd, J=8.7, 2.4 Hz, 1H), 5.27 (s, 2H), 3.70 (s, 3H). $^{13}$C NMR (126 MHz, DMSO-d$_6$, TMS, ppm) δ=21.08, 39.01, 47.64, 55.18, 100.18, 103.36, 112.12, 112.53, 124.56, 126.33, 126.55, 126.77, 127.21, 127.29, 128.60, 130.97, 138.16, 138.21, 153.89.

Example 19. 3-(1-ethyl-1H-imidazol-5-yl)-4-methoxy-1H-indole

The compound was synthesized from 4-methoxyindole-3-carbaldehyde (3 mmol) and ethylamine according to the general procedure 1 and purified via trituration with hexane: isopropanol 2:1 mixture (46% yield).

LC-MS: m/z=241.83; $t_R$=1.34 min. $^1$H NMR (500 MHz, DMSO-$d_6$) δ 11.38 (s, 1H), 7.69 (s, 1H), 7.23 (s, 1H), 7.09-7.01 (m, 2H), 6.75 (d, J=1.2 Hz, 1H), 6.52 (dd, J=5.7, 2.9 Hz, 1H), 3.84 (q, J=7.3 Hz, 2H), 3.68 (s, 3H), 2.08 (s, 1H), 1.14 (t, J=7.3 Hz, 3H). $^{13}$C NMR (126 MHz, DMSO) δ 153.75, 138.39, 136.72, 128.02, 127.53, 125.20, 122.95, 117.08, 105.68, 103.09, 100.33, 55.46, 31.17, 16.30.

Example 20. 3-(1-ethyl-1H-imidazol-5-yl)-7-methyl-1H-indole

The compound was synthesized from 7-methylindole-3-carbaldehyde (3 mmol) and ethylamine according to the general procedure 1 and purified via trituration with hexane: isopropanol 2:1 mixture (47% yield).

LC-MS: m/z=225.90; $t_R$=1.85 min. $^1$H NMR (500 MHz, DMSO-$d_6$, TMS, ppm) δ=11.40 (s, 1H), 7.76 (d, J=1.1 Hz, 1H), 7.50 (d, J=2.6 Hz, 1H), 7.36-7.27 (m, 1H), 7.03-6.92 (m, 3H), 4.00 (q, J=7.3 Hz, 2H), 2.50 (d, J=0.8 Hz, 1H), 1.27-1.14 (m, 3H). $^{13}$C NMR (126 MHz, DMSO-$d_6$, TMS, ppm) δ=16.22, 16.77, 16.78, 39.01, 40.01, 104.26, 116.43, 119.50, 119.75, 120.98, 122.12, 123.85, 125.87, 126.21, 127.17, 135.53, 136.93.

Example 21. 3-(1-ethyl-1H-imidazol-5-yl)-5-methoxy-2-methyl-1H-indole

The compound was synthesized from 5-methoxy-2-methylindole-3-carbaldehyde (3 mmol) and ethylamine according to the general procedure 1 and purified via column chromatography (SiO$_2$, AcOEt:MeOH 49:1) (45% yield).

LC-MS: m/z=256.16; $t_R$=1.22 min. $^1$H NMR (500 MHz, DMSO-$d_6$, TMS, ppm) δ=11.16 (s, 1H), 7.81 (d, J=1.1 Hz, 1H), 7.23 (dd, J=8.7, 0.6 Hz, 1H), 6.82 (d, J=1.2 Hz, 1H), 6.69 (dd, J=8.7, 2.5 Hz, 1H), 6.59 (d, J=2.4 Hz, 1H), 3.78 (q, J=7.2 Hz, 2H), 3.68 (s, 3H), 2.26 (s, 3H), 1.12 (t, J=7.3 Hz, 3H). $^{13}$C NMR (126 MHz, DMSO-$d_6$, TMS, ppm) δ=153.70, 137.10, 135.91, 130.20, 128.79, 128.32, 125.19, 111.60, 110.42, 100.44, 99.56, 55.22, 39.30, 16.37, 11.90.

Example 22. 3-(1-ethyl-1H-imidazol-5-yl)-1H-indole

The compound was synthesized from indole-3-carbaldehyde (5 mmol) and ethylamine according to the general procedure 1 and purified via flash chromatography (SiO$_2$, CHCl$_3$:MeOH 19:1) (89% yield).

LC-MS: m/z=211.70; $t_R$=0.86 min. $^1$H NMR (500 MHz, DMSO-$d_6$, TMS, ppm) δ=11.52 (s, 1H), 7.81 (d, J=1.1 Hz, 1H), 7.58-7.46 (m, 3H), 7.18 (ddd, J=8.1, 6.9, 1.1 Hz, 1H), 7.12-7.02 (m, 2H), 4.03 (q, J=7.2 Hz, 2H), 1.24 (t, J=7.3 Hz, 3H). $^{13}$C NMR (126 MHz, DMSO-$d_6$, TMS, ppm) δ=16.70, 40.32, 40.49, 104.28, 112.30, 119.33, 119.98, 120.05, 122.15, 124.63, 124.85, 126.27, 126.96, 127.60, 128.81, 136.54, 137.45.

Example 23. 5-methoxy-3-[1-(3-methoxypropyl)-1H-imidazol-5-yl]-1H-indole

The compound was synthesized from 5-methoxyindole-3-carbaldehyde (3 mmol) and 3-methoxypropylamine according to the general procedure 1 and purified via trituration with diethyl ether:acetone 2:1 mixture (45% yield).

LC-MS: m/z=286.08; $t_R$=0.47-1.30 min. $^1$H NMR (500 MHz, DMSO-$d_6$, TMS, ppm) δ 11.28 (s, 1H), 7.72 (d, J=1.1 Hz, 1H), 7.48 (d, J=2.6 Hz, 1H), 7.34 (dd, J=8.7, 0.6 Hz, 1H), 7.02 (d, J=1.1 Hz, 1H), 6.92 (d, J=2.4 Hz, 1H), 6.80 (dd, J=8.7, 2.4 Hz, 1H), 4.03 (t, 2H), 3.74 (s, 3H), 3.19 (t, J=6.0 Hz, 2H), 3.11 (s, 3H), 1.79 (p, J=7.3, 6.1 Hz, 2H). $^{13}$C NMR (126 MHz, DMSO-$d_6$, TMS, ppm) δ=153.87, 137.60, 131.04, 127.13, 126.89, 126.01, 124.68, 112.52, 112.00, 103.54, 100.17, 68.55, 57.77, 55.24, 41.65, 30.29.

Example 24. 5-benzyloxy-3-(1-ethyl-1H-imidazol-5-yl)-1H-indole

The compound was synthesized from 5-benzyloxyindole-3-carbaldehyde (3 mmol) and ethylamine according to the general procedure 1, except for the fact that it precipitated out of solution during the reaction and the reaction mixture was vacuum filtered instead of being extracted. The obtained solid was washed with 2×5 ml cold MeOH (85% yield).

LC-MS: m/z=318.01; $t_R$=2.29 min. $^1$H NMR (500 MHz, DMSO-$d_6$, TMS, ppm) δ=11.32-11.27 (m, 1H), 7.75 (d, J=1.1 Hz, 1H), 7.52-7.46 (m, 2H), 7.46-7.41 (m, 1H), 7.43-7.34 (m, 3H), 7.34-7.26 (m, 1H), 7.01 (d, J=2.4 Hz, 1H), 6.97 (d, J=1.1 Hz, 1H), 6.89 (dd, J=8.7, 2.4 Hz, 1H), 5.09 (s, 2H), 3.96 (q, J=7.2 Hz, 2H), 1.20 (t, J=7.2 Hz, 3H). $^{13}$C NMR (126 MHz, DMSO-$d_6$, TMS, ppm) δ=16.20, 39.01, 69.62, 101.89, 103.64, 112.58, 112.68, 124.76, 125.82, 126.75, 126.76, 127.01, 127.48, 127.54, 128.30, 131.21, 136.88, 137.72, 152.82, 152.82.

Example 25. 3-(1-ethyl-1H-imidazol-5-yl)-7-fluoro-5-iodo-1H-indole

The compound was synthesized from 7-fluoro-5-iodoindole-3-carbaldehyde (1.1 mmol) and ethylamine according to the general procedure 1 and purified via trituration with hexane:isopropanol 2:1 mixture (59% yield).

LC-MS: m/z=355.60; $t_R$=2.11 min. $^1$H NMR (500 MHz, DMSO-$d_6$, TMS, ppm) δ=12.19 (s, 1H), 7.79 (d, J=1.1 Hz, 1H), 7.64 (s, 1H), 7.60 (d, J=1.3 Hz, 1H), 7.34 (dd, J=10.4, 1.3 Hz, 1H), 7.02 (d, J=1.1 Hz, 1H), 3.97 (q, J=7.3 Hz, 2H), 1.19 (t, 3H). $^{13}$C NMR (126 MHz, DMSO-$d_6$, TMS, ppm) δ=149.99, 148.00, 137.46, 132.51, 127.87, 126.40, 123.59, 123.50, 115.03, 104.23, 81.44, 39.48, 16.15.

Example 26. 3-(1-ethyl-1H-imidazol-5-yl)-1H-indole-5-carboxamide

The compound was synthesized from 3-(1-ethyl-1H-imidazol-5-yl)-1H-indole-5-carbonitrile, the nitrile group hydrolysis was accomplished according to a modified procedure outlined by Agarwal et al.[35]

A suspension of 3-(1-ethyl-1H-imidazol-5-yl)-1H-indole-5-carbonitrile (3.4 mmol, 0.8 g) in 1 ml MeOH and 5 ml THF was stirred in an ice-salt bath for 15 minutes until 0° C. was reached. Hydrogen peroxide (30% solution, 5.4 ml) was added dropwise while keeping the temperature below 10° C. Stirring was continued for 15 minutes and sodium hydroxide (20% solution, 5.4 ml) was added dropwise keeping temperature below 10° C. The mixture was allowed to warm to room temperature and stirred for 24 hours. The product was extracted from the reaction mixture with chloroform and purified by trituration with acetone. Yield: 9%

LC-MS: m/z=255.1; $t_R$=0.5 min. $^1$H NMR (500 MHz, DMSO-$d_6$, TMS, ppm) δ=8.11 (d, J=1.7 Hz, 1H), 7.95 (s, 1H), 7.79 (s, 1H), 7.74 (dd, J=8.6, 1.7 Hz, 1H), 7.61 (d, J=1.7 Hz, 1H), 7.47 (dd, J=8.5, 0.6 Hz, 1H), 7.10 (d, J=7.9 Hz, 1H), 4.02 (q, J=7.2 Hz, 2H), 2.08 (s, 3H), 1.22 (t, J=7.2 Hz, 2H). $^{13}$C NMR (126 MHz, DMSO-$d_6$, TMS, ppm)

δ=168.84, 137.59, 137.17, 127.69, 125.99, 125.90, 125.24, 125.20, 121.67, 119.09, 111.22, 105.05, 30.70, 16.20.

Example 27. 3-(1-cyclopropyl-1H-imidazol-5-yl)-5-iodo-1H-indole

The compound was synthesized from 5-iodoindole-3-carbaldehyde (3 mmol) and cyclopropylamine according to the general procedure 1 and purified via trituration with hexane:isopropanol 2:1 mixture (22% yield).

LC-MS: m/z=349.94; $t_R$=2.14 min. $^1$H NMR (500 MHz, DMSO-$d_6$, TMS, ppm) δ=11.61 (s, 1H), 7.93 (d, J=1.6 Hz, 1H), 7.71 (dd, 2H), 7.42 (dd, J=8.5, 1.7 Hz, 1H), 7.32 (dd, J=8.4, 0.6 Hz, 1H), 7.09 (d, J=1.1 Hz, 1H), 3.48-3.40 (m, 1H), 0.97-0.81 (m, 4H). $^{13}$C NMR (126 MHz, DMSO-$d_6$, TMS, ppm) δ=137.40, 134.97, 129.62, 128.55, 127.37, 127.28, 126.55, 124.93, 114.24, 103.63, 83.40, 27.03, 6.90.

Example 28. 5-methoxy-3-[1-(2-phenylethyl)-1H-imidazol-5-yl]-1H-indole

The compound was synthesized from 5-methoxyindole-3-carbaldehyde (3 mmol) and 2-phenylethylamine according to the general procedure 1 and purified via trituration with hexane:isopropanol 2:1 mixture (61% yield).

LC-MS: m/z=318.21; $t_R$=2.09 min. $^1$H NMR (500 MHz, DMSO-$d_6$, TMS, ppm) δ=11.32 (s, 1H), 7.61 (d, J=1.1 Hz, 1H), 7.44 (d, J=2.6 Hz, 1H), 7.37 (d, J=8.7 Hz, 1H), 7.27-7.18 (m, 2H), 7.21-7.13 (m, 1H), 7.01 (dt, J=7.0, 1.4 Hz, 3H), 6.94 (d, J=2.4 Hz, 1H), 6.82 (dd, J=8.8, 2.4 Hz, 1H), 4.21 (t, 2H), 3.74 (s, 3H), 2.85 (t, J=8.1, 6.7 Hz, 2H). $^{13}$C NMR (126 MHz, DMSO) δ 153.91, 138.08, 137.56, 131.08, 128.54, 128.35, 128.33, 128.26, 127.24, 126.97, 126.40, 125.86, 124.84, 112.59, 112.05, 103.59, 100.18, 55.27, 45.82, 36.23.

Example 29. 2-(1-methyl-1H-imidazol-5-yl)-1H-indole

The compound was synthesized from indole-2-carbaldehyde (3 mmol) and methylamine according to the general procedure 1 and purified via column chromatography (SiO$_2$, CHCl$_3$:MeOH 49:1) (10% yield).

LC-MS: m/z=198.04; $t_R$=1.07 min. $^1$H NMR (500 MHz, DMSO-$d_6$, TMS, ppm) δ=11.34 (s, 1H), 7.76-7.71 (m, 1H), 7.54 (ddt, J=7.8, 1.3, 0.8 Hz, 1H), 7.40-7.30 (m, 2H), 7.10 (ddd, J=8.1, 7.0, 1.2 Hz, 1H), 7.00 (ddd, J=7.9, 7.1, 1.0 Hz, 1H), 6.66 (dd, J=2.2, 0.9 Hz, 1H), 3.83 (d, J=0.5 Hz, 3H). $^{13}$C NMR (126 MHz, DMSO-$d_6$, TMS, ppm) δ=32.92, 39.00, 40.01, 98.99, 110.93, 119.28, 119.87, 121.58, 125.77, 127.57, 127.63, 128.42, 136.29, 139.92.

Example 30. 5-(1-ethyl-1H-imidazol-5-yl)-1H-indole

The compound was synthesized from indole-5-carbaldehyde (3 mmol) and ethylamine according to the general procedure 1 and purified via flash chromatography (SiO$_2$, CHCl$_3$:MeOH 49:1) (23% yield). LC-MS: m/z=211.90; $t_R$=0.49-0.79 min. $^1$H NMR (500 MHz, DMSO-$d_6$, TMS, ppm) δ 11.27 (s, 1H), 7.75 (s, 1H), 7.60 (s, 1H), 7.56-7.32 (m, 3H), 7.21-7.12 (m, 1H), 6.92 (d, J=1.2 Hz, 1H), 6.50 (s, 1H), 4.11-3.94 (m, 3H), 1.21 (t, J=7.2 Hz, 4H). $^{13}$C NMR (126 MHz, DMSO-$d_6$, TMS, ppm) δ 137.25, 135.36, 133.52, 127.41, 126.70, 126.17, 121.87, 120.58, 120.08, 111.63, 101.33, 39.43, 16.26.

Example 31. 6-(1-ethyl-1H-imidazol-5-yl)-1H-indole

The compound was synthesized from indole-6-carbaldehyde (3 mmol) and ethylamine according to the general procedure 1 and purified via flash chromatography (SiO$_2$, CHCl$_3$, then CHCl$_3$:MeOH 49:1) (20% yield).

LC-MS: m/z=211.77; $t_R$=1.46 min. $^1$H NMR (500 MHz, DMSO-$d_6$, TMS, ppm) δ=11.20 (s, 1H), 7.75 (d, J=1.1 Hz, 1H), 7.61 (dd, J=8.1, 0.8 Hz, 1H), 7.46-7.37 (m, 2H), 7.05 (dd, J=8.1, 1.5 Hz, 1H), 6.93 (d, J=1.2 Hz, 1H), 6.47 (ddd, J=2.9, 1.9, 0.9 Hz, 1H), 4.05 (q, J=7.2 Hz, 1H), 1.22 (t, J=7.2 Hz, 3H). $^{13}$C NMR (126 MHz, DMSO-$d_6$, TMS, ppm) δ=16.33, 39.01, 101.06, 111.21, 119.64, 120.25, 122.56, 126.28, 126.90, 127.17, 133.35, 135.92, 137.58.

Example 32. 3-(1H-imidazol-5-yl)-1H-indole

The compound was synthesized by hydrogenation of 3-(1-benzyl-1H-imidazol-5-yl)-5-methoxy-1H-indole (Example 18) over palladium on carbon. The substrate was dissolved in methanol in a pressure reactor, 10 mol % Pd/C was added. The reactor was sealed and pressurized to 7 bar with H$_2$. Completion of the reaction was monitored with LC-MS. The mixture was then filtered through Celite which was then washed with MeOH. Solvent was stripped off on a rotary evaporator and the resulting solid was triturated under hexane:isopropanol:acetone 3:1:1 mixture. Yield: 95%

LC-MS: m/z=214.10; $t_R$=0.5-0.7 min.

Example 33. 4-fluoro-5-iodo-3-(1-methyl-1H-imidazol-5-yl)-1H-indole

The compound was synthesized from 4-fluoro-5-iodo-1H-indole-3-carbaldehyde (8.89 mmol) and methylamine according to the general procedure 1 and purified via trituration with hexane:isopropanol 2:1 mixture (77% yield). The hydrochloride of the compound was formed by dissolving the free base in a small amount (5-10 ml) of isopropyl alcohol, adding 1.2 eq. of 20% hydrogen chloride solution in isopropanol and adding sufficient amount of diethyl ether to produce permanent turbidity (40-60 ml). The precipitated salt was suction filtered and vacuum dried (954 mg, 70% yield).

LC-MS: m/z=341.79; $t_R$=1.93 min.

Example 34. 3-(1-ethyl-1H-imidazol-5-yl)-4-fluoro-5-iodo-1H-indole

The compound was synthesized from 4-fluoro-5-iodo-1H-indole-3-carbaldehyde (1.5 mmol) and ethylamine according to the general procedure 1 and purified via trituration with hexane:isopropanol 2:1 mixture (57% yield). The hydrochloride of the compound was formed by dissolving the free base in a small amount of isopropyl alcohol, adding 1.2 eq. of 20% hydrogen chloride solution in isopropanol and adding sufficient amount of diethyl ether to produce permanent turbidity. The precipitated salt was suction filtered and vacuum dried (259 mg, 81% yield).

LC-MS: m/z=355.84; $t_R$=2.01 min.

Example 35. 5-bromo-3-(1-ethyl-1H-imidazol-5-yl)-4-fluoro-1H-indole

The compound was synthesized from 5-bromo-4-fluoro-1H-indole-3-carbaldehyde (0.56 mmol) and ethylamine according to the general procedure 1 and purified via trituration with hexane:isopropanol 2:1 mixture (9 mg, 5% yield).

LC-MS: m/z=307.94 and 309.94; $t_R$=1.86 min.

Example 36. 3-(1-ethyl-1H-imidazol-5-yl)-4-fluoro-1H-indole-5-carboxamide

The compound was synthesized from the intermediate 4-fluoro-3-(1-ethyl-1H-imidazol-5-yl)-1H-indole-5-carbonitrile, the nitrile group hydrolysis was accomplished according to a modified procedure outlined by Agarwal et al.[35]

A suspension of 4-fluoro-3-(1-ethyl-1H-imidazol-5-yl)-1H-indole-5-carbonitrile (1 mmol) in 0.5 ml MeOH and 2.5 ml THF was stirred in an ice-salt bath for 15 minutes until 0° C. was reached. Hydrogen peroxide (30% solution, 2.5 ml) was added dropwise while keeping the temperature below 10° C. Stirring was continued for 15 minutes and sodium hydroxide (20% solution, 2.5 ml) was added dropwise keeping temperature below 10° C. The mixture was allowed to warm to room temperature and stirred for 48 hours. The product was extracted from the reaction mixture with chloroform and purified by trituration with acetone. Yield: 32%

LC-MS: m/z=273.16; $t_R$=0.45 min.

Example 37. 4-fluoro-3-(1-methyl-1H-imidazol-5-yl)-1H-indole-5-carboxamide

The compound was synthesized from the intermediate 4-fluoro-3-(1-methyl-1H-imidazol-5-yl)-1H-indole-5-carbonitrile, the nitrile group hydrolysis was accomplished according to a modified procedure outlined by Agarwal et al.[35]

A suspension of 4-fluoro-3-(1-methyl-1H-imidazol-5-yl)-1H-indole-5-carbonitrile (1 mmol) in 0.5 ml MeOH and 2.5 ml THF was stirred in an ice-salt bath for 15 minutes until 0° C. was reached. Hydrogen peroxide (30% solution, 2.5 ml) was added dropwise while keeping the temperature below 10° C. Stirring was continued for 15 minutes and sodium hydroxide (20% solution, 2.5 ml) was added dropwise keeping temperature below 10° C. The mixture was allowed to warm to room temperature and stirred for 48 hours. The product was extracted from the reaction mixture with chloroform and purified by trituration with acetone (24% yield). LC-MS: m/z=259.10; $t_R$=0.46 min.

Example 38. 4-fluoro-3-(1-ethyl-1H-imidazol-5-yl)-1H-indole

The compound was synthesized from 4-fluoro-1H-indole-3-carbaldehyde (1 mmol) and ethylamine according to the general procedure 1 and purified via trituration with hexane:isopropanol 2:1 mixture (44% yield).

LC-MS: m/z=230.10; $t_R$=0.48-1.18 min.

Intermediates 1-methyl-1H-indole-3-carbaldehyde

The compound was synthesized from 1H-indole-3-carbaldehyde (10 g, 68.9 mmol) according to the general procedure 3 (80% yield)

LC-MS: m/z=159.83 $t_R$=2.09

5-methoxy-1H-indole-3-carbaldehyde

The compound was synthesized from 5-methoxy-1H-indole (170 mmol) according to the general procedure 2, with the exception that it was scaled up proportionally to the 5-methoxyindole (69% yield).

LC-MS: m/z=176.11; $t_R$=2.20 min.

5-fluoro-1H-indole-3-carbaldehyde

The compound was synthesized from 5-fluoro-1H-indole (22 mmol) according to the general procedure 2 (70% yield).

LC-MS: m/z=163.78; $t_R$=1.97 min.

5-iodo-1H-indole-3-carbaldehyde

The compound was synthesized from 5-iodo-1H-indole (22 mmol) according to the general procedure 2 (90% yield).

LC-MS: m/z=271.75; $t_R$=2.62 min.

5-methyl-1H-indole-3-carbaldehyde

The compound was synthesized from 5-methyl-1H-indole (22 mmol) according to the general procedure 2 (88% yield).

LC-MS: m/z=160.05; $t_R$=2.15 min.

5-iodo-7-fluoro-1H-indole-3-carbaldehyde

The compound was synthesized from 5-iodo-7-fluoro-1H-indole (1.88 mmol) according to the general procedure 2, with the exception that it was scaled down proportionally to 5-iodo-7-fluoroindole (75% yield).

LC-MS: m/z=289.82; $t_R$=2.88 min.

4-bromo-1H-indole-3-carbaldehyde

The compound was synthesized from 4-bromo-1H-indole (22 mmol) according to the general procedure 2 (53% yield).

LC-MS: m/z=223.97 and 226.03; $t_R$=2.49 min.

5-cyano-1H-indole-3-carbaldehyde

The compound was synthesized from 5-cyano-1H-indole (22 mmol) according to the general procedure 2 with an exception—no NaOH solution was added after quenching the Vilsmeier adduct with water to avoid nitrile hydrolysis (84% yield).

LC-MS: m/z=170.9; $t_R$=1.66 min.

5-chloro-1H-indole-3-carbaldehyde

The compound was synthesized from 5-chloro-1H-indole (22 mmol) according to the general procedure 2 (48% yield).

LC-MS: m/z=179.71; $t_R$=2.37 min.

4-fluoro-1H-indole-3-carbaldehyde

The compound was synthesized from 4-fluoro-1H-indole (22 mmol) according to the general procedure 2 (73% yield).

LC-MS: m/z=164.12; $t_R$=1.94 min.

4-fluoro-5-iodo-1H-indole 4-fluoroindole (36 g) was suspended in 67 ml EtOH and mixed with sodium metabisulphite (62 g) dissolved in 210 ml distilled water for three days. The resulting slurry of sodium 4-fluoro-1H-indole-2-sulfonate was suction filtered, washed with 2×60 ml EtOH and 2×60 ml diethyl ether and vacuum dried (62.47 g, 91% yield). The dry adduct (4-fluoro-1H-indole-2-sulfonate, 22 g) was suspended in 140 ml of acetic anhydride and heated to 70° C. After two hours, the temperature was raised to 90° C. for 30 min and the mixture was left to cool to room temperature. The precipitated sodium 1-acetyl-4-fluoro-1H-indole-2-sulfonate was vacuum filtered, washed with diethyl ether (4×50 ml) and vacuum dried at 40° C. (yield 22.5 g, 88%). To a one-litre round bottom flask there were added: distilled water (37 ml), potassium iodide (12.3 g), sodium 1-acetyl-4-fluoro-1H-indole-2-sulfonate (9.2 g, 68.1 mmol) from the previous step. With vigorous stirring, iodine chloride (9.2 ml) was added dropwise. The mixture was left for 24 h after which the contents of the flask solidified. There was added sodium metabisulphite (70 ml 20% solution), the contents were mixed until full discoloration was achieved followed by the addition of sodium hydroxide (65 ml 30%) and the crude 4-fluoro-5-iodo-1H-indole was vacuum filtered and air dried. The crude product was recrystallized from petroleum ether (100° C.–140° C. fraction) to yield pure 4-fluoro-5-iodo-1H-indole (6.577 g, 37% yield).

LC-MS: m/z=261.9; $t_R$=3.36 min.

4-fluoro-5-iodo-1H-indole-3-carbaldehyde

The compound was synthesized from 4-fluoro-5-iodo-1H-indole (1 g, 3.83 mmol) according to the general procedure 2 (754 mg, 67% yield).

LC-MS: m/z=289.68; $t_R$=2.68 min.

4-fluoro-1H-indole-5-carbonitrile 4-fluoro-5-iodo-1H-indole (7 g, 26.8 mmol), copper cyanide (3.84 g, 1.6 eq.) and 30 ml N-methylpyrrolidone were placed in a sealed pressure tube under argon atmosphere, heated to 200° C. and kept at this temperature for 10 h. The mixture was suspended in 30 ml 25% ammonia solution, filtered through celite, washed 2×25 ml of 10% ammonia solution, 4×25 ml $H_2O$, and the celite was thoroughly washed 5×25 ml $CHCl_3$. The combined organic washings were filtered through a bed of silica gel, evaporated on rotary evaporator and purified by flash chromatography using $CHCl_3$ as eluent (3 g, 70% yield).

LC-MS: m/z=189.08; $t_R$=1.90 min.

4-fluoro-3-formyl-1H-indole-5-carbonitrile

The compound was synthesized from 4-fluoro-1H-indole-5-carbonitrile (14.86 mmol) according to the general procedure 2 (2.38 g, 81% yield).

LC-MS: m/z=160.70; $t_R$=2.79 min.

4-fluoro-3-(1-ethyl-1H-imidazol-5-yl)-1H-indole-5-carbonitrile

The compound was synthesized from 4-fluoro-3-formyl-1H-indole-5-carbonitrile (1 g, 5.31 mmol) and ethylamine according to the general procedure 1 and purified via trituration with hexane:isopropanol 2:1 mixture (1.06 g, 79% yield).

LC-MS: m/z=255.03; $t_R$=0.48-0.99 min.

4-fluoro-3-(1-methyl-1H-imidazol-5-yl)-1H-indole-5-carbonitrile

The compound was synthesized from 4-fluoro-3-formyl-1H-indole-5-carbonitrile (1 g, 5.31 mmol) and ethylamine according to the general procedure 1 and purified via trituration with hexane:isopropanol 2:1 mixture (0.883 g, 69% yield).

LC-MS: m/z=240.98; $t_R$=0.49-0.76 min.

Cell Cultures

HEK293 cells stably expressing the human serotonin 5-$HT_{1A}$R, 5-$HT_6$ and 5-$HT_{7b}$R receptors (obtained using of Lipofectamine 2000, Invitrogen), or CHO-K1 cells with plasmid containing the sequence coding for the human serotonin 5-$HT_{7A}$ receptor (Perkin Elmer) were maintained at 37° C. in a humidified atmosphere with 5% $CO_2$ and were grown in Dulbecco's Modified Eagle's Medium containing 10% dialyzed foetal bovine serum and 500 µg/ml G418 sulphate. For membrane preparations, cells were subcultured into 150 $cm^2$ cell culture flasks, grown to 90% confluence, washed twice with phosphate buffered saline (PBS) pre-warmed to 37° C. and were pelleted by centrifugation (200 g) in PBS containing 0.1 mM EDTA and 1 mM dithiothreitol, and stored at −80° C.

5-$HT_{1A}$/5-$HT_{2A}$/5-$HT_6$/5-$HT_7$ Radioligand Binding Assays

The cell pellets were thawed and homogenized in 10 volumes of assay buffer using an Ultra Turrax tissue homogenizer and centrifuged twice at 35,000 g for 15 min at 4° C., with incubation for 15 min at 37° C. in between the rounds of centrifugation. The composition of buffers and experimental procedure of all the assays are summarized in Table 1. Each compound was tested in triplicate at 7-8 concentrations ($10^{-11}$-$10^{-4}$ M). The inhibition constants ($K_i$) were calculated using the Cheng-Prusoff[36] equation, and the results were expressed as the means of at least two independent experiments.

TABLE 1

Experimental details of 5-$HT_{1A}$, 5-$HT_{2A}$, 5-$HT_6$, and 5-$HT_7$ receptor binding affinity assays. Full experimental procedures are available in literature referenced in the last row.

|  | 5-$HT_{1A}$ | 5-$HT_{2A}$ | 5-$HT_6$ | 5-$HT_7$ |
| --- | --- | --- | --- | --- |
| Source | Human recombinant (HEK293 cells) | Human recombinant (CHO-K1 cells) | Human recombinant (HEK293 cells) | Human recombinant (HEK293 cells) |
| Radioligand | [$^3$H]-8-OH-DPAT | [$^3$H]-Ketanserin | [$^3$H]-LSD | [$^3$H]-5-CT |
| Radioligand $K_d$ (nM) | 2.5 | 1 | 1.9 | 0.8 |
| Non specific | 5-HT (10 µM) | Mianserin (20 µM) | Methiothepin y (10 µM) | 5-HT (10 µM) |
| Incubation | 60 min/RT | 60 min/27° C. | 60 min/37° C. | 60 min/37° C. |
| Reference compound | Buspirone ($K_i$: 22 nM) | Olanzapine ($K_i$: 4 nM) | Olanzapine ($K_i$: 7 nM) | Clozapine ($K_i$: 30 nM) |
| References | 37 | 38 | 37 | 37 |

$\alpha_1$, $\alpha_2$, $CB_1$, $D_3$, $H_1$, 5-$HT_{1B}$, 5-$HT_{2B}$, 5-$HT_{5A}$ Radioligand Binding Assays The experimental details: source of the receptor, radioligand, concentration of the radioligand, binding constant of the radioligand ($K_d$), incubation time, the reference compound and a reference to full experimental procedure of all the assays are summarized in Table 2. In all the experiments, a specific radioligand exhibiting high affinity for a given receptor was displaced by the tested compound.

TABLE 2

Experimental details of $\alpha_1$, $\alpha_{2C}$, $CB_1$, $D_3$, $H_1$, 5-HT$_{1B}$, 5-HT$_{2B}$, and 5-HT$_{5A}$ receptor binding affinity assays (performed at Eurofins Cerep, http://www.cerep.fr/). Full experimental procedures are available in literature referenced in the last row.

| | $\alpha_1$ | $\alpha_{2C}$ | $CB_1$ | $D_3$ | $H_1$ | 5-HT$_{1B}$ | 5-HT$_{2B}$ | 5-HT$_{5A}$ |
|---|---|---|---|---|---|---|---|---|
| Source | Rat cerebral cortex | Human recombinant (CHO cells) | Human recombinant (CHO cells) | Human recombinant (CHO cells) | Human recombinant (HEK293 cells) | Rat cerebral cortex | Human recombinant (CHO cells) | Human recombinant (HEK293 cells) |
| Radioligand | [$^3$H]-prazosin | [$^3$H]-RX 821002 | [$^3$H]-CP 55940 | [$^3$H]-methyl-spiperone | [$^3$H]-pyrilamine | [$^{125}$I]-CYP (+30 µM iso-proterenol) | [$^{125}$I]-(±DOI) | [$^3$H]-LSD |
| Radioligand K$_d$ (nM) | 0.09 | 0.95 | 3.5 | 0.085 | 1.7 | 0.16 | 0.2 | 1.5 |
| Non specific | Prazosin 0.5 µM | (−)epinephrine (100 µM) | WIN 55212-2 (10 µM) | (+)butaclamol (10 µM) | Pyrilamine (1 µM) | Serotonin (10 µM) | (±DOI) (1 µM) | Serotonin (100 µM) |
| Incubation | 60 min/RT | 60 min/RT | 120 min/37° C. | 60 min/RT | 60 min/RT | 120 min/37° C. | 60 min/RT | 120 min/37° C. |
| Reference compound | Prazosin (IC$_{50}$: 0.182 nM) | Yohimbine (IC$_{50}$: 1.9 nM) | CP 55940 (IC$_{50}$: 0.58 nM) | (+) butaclamol (IC$_{50}$: 1.4 nM) | Pyrilamine (IC$_{50}$: 2.2 nM) | Serotonin (IC$_{50}$: 10 nM) | (±DOI) (IC$_{50}$: 5 nM) | Serotonin (IC$_{50}$: 120 nM) |
| References | 39 | 40 | 41 | 42 | 43 | 44 | 45 | 46 |

Functional Assays

The functional properties of compounds in HEK293 cells overexpressing 5-HT$_7$R were evaluated to study their ability to increase cAMP production for the studied compounds. Each compound was tested at 8 concentrations in the range of $10^{-11}$-$10^{-4}$ M. Cells (prepared with the use of Lipofectamine 2000) were maintained at 37° C. in a humidified atmosphere with 5% $CO_2$ and were grown in DMEM containing 10% dialyzed (FBA) and 500 µg/ml G418 sulphate. For the functional experiments, the cells were subcultured in 25 cm$^2$ diameter dishes, grown to 90% confluence, washed twice with PBS pre-warmed to 37° C. and centrifuged for 5 min (160×g$_0$). The supernatant was aspirated, the cell pellet was re-suspended in stimulation buffer (1×HBSS, 5 mM HEPES, 0.5 mM IBMX, and 0.1% BSA). The total cAMP was measured using the LANCE cAMP detection kit (PerkinElmer), according to the manufacturer's directions. For the cAMP level quantification, cells (5 µl) were incubated with compounds (5 µl) for 30 min at room temperature in a 384-well white opaque microtiter plate. After incubation, 10 µl working solution (5 µl Eu-cAMP and 5 µl ULight-anti-cAMP) was added to stop the reaction and induce cells lysis. The assay plate was incubated for 1 h at room temperature, and time-resolved fluorescence resonance energy transfer (TR-FRET) was detected by an Infinite M1000 Pro (Tecan, Männedorf, Switzerland) using instrument settings from the LANCE cAMP detection kit manual.

Physicochemical Parameters Calculations

CNS MPO parameter was calculated according to Wager et al.[46] The physicochemical parameters: TPSA, log P, log D, were calculated using Chem Axon Instant JChem software. These results are summarized in Table 3 as a complement to the biochemical results.

TABLE 3

Biochemical and physicochemical characteristics of the inventive compounds

| Example No. | pK$_i$ 5-HT$_{1A}$R | pK$_i$ 5-HT$_7$R | 5-HT$_7$ EC$_{50}$ [nM] | CNS MPO |
|---|---|---|---|---|
| 1 | 5.35 | 6.41 | ND | 3.44 |
| 2 | 6.07 | 7.26 | 150 | 3.96 |
| 3 | 4.97 | 5.25 | ND | 4.38 |
| 4 | 6.18 | 7.52 | 60 | 4.97 |
| 5 | 5.68 | 7.19 | ND | 5.28 |
| 6 | 6.18 | 6.49 | ND | 5.28 |
| 7 | 5.89 | 5.48 | ND | 5.30 |
| 8 | 6.27 | 6.87 | ND | 5.30 |
| 9 | 4.36 | 4.97 | ND | 4.99 |
| 10 | 4.34 | 5.64 | ND | 5.00 |
| 11 | 5.63 | 6.52 | ND | 4.57 |
| 12 | 5.04 | 7.38 | 149 | 4.90 |
| 13 | 5.91 | 7.70 | 154 | 4.99 |
| 14 | 5.98 | 8.22 | 19 | 4.99 |
| 15 | 3.98 | 5.6 | ND | 5.41 |
| 16 | 5.67 | 7.36 | 45 | 4.22 |
| 17 | 6.54 | 7.41 | 22 | 4.26 |
| 18 | 4.4 | 4.62 | ND | 5.30 |
| 19 | 5.13 | 6.91 | ND | 5.01 |
| 20 | ND | 5.05 | ND | 4.49 |
| 21 | ND | 4.7 | ND | 5.28 |
| 22 | 4.59 | 6.27 | ND | 4.22 |
| 23 | 4.91 | 5.67 | ND | 4.77 |
| 24 | 4.46 | 5.43 | ND | 5.28 |
| 25 | 6.17 | 7.44 | ND | 4.98 |
| 26 | 6.91 | 8.30 | ND | 3.00 |
| 27 | 5.57 | 6.23 | ND | 3.00 |
| 28 | 5.53 | 5.96 | ND | 5.28 |
| 29 | 4.49 | 4.04 | ND | 3.27 |
| 30 | 4.79 | 5.28 | ND | 4.12 |
| 31 | 4.55 | 5.58 | ND | 4.13 |
| 32 | 5.17 | 5.92 | ND | 2.26 |
| 33 | 6.37 | 8.70 | ND | 5.12 |
| 34 | 6.23 | 8.40 | ND | 5.12 |
| 35 | 6.50 | 7.80 | ND | 3.68 |
| 36 | 6.03 | 7.66 | ND | 3.50 |
| 37 | 5.76 | 7.74 | ND | 5.12 |
| 38 | 5.25 | 6.41 | ND | 4.70 |

The compounds of the invention exhibit very high selectivity towards the 5-HT$_7$ serotonin receptor over the other related CNS targets, with the exception for 5-HT$_{7B}$, towards which they are moderately selective.

Two compounds, examples 4 and 14 were selected for additional CNS-target screening (at two concentrations, $10^{-6}$ and $10^{-8}$ M) in order to check their selectivity over $\alpha_1$, $\alpha_{2C}$, $CB_1$, $D_3$, $H_1$, 5-HT$_{1B}$, 5-HT$_{2B}$, 5-HT$_{5A}$ receptors. The results are summarized in Table 3.

TABLE 4

CNS pharmacology panel for the selected compounds (Example 4 and Example 14).

| Ex. No. | Concentration [M] | % of inhibition of reference compound at given receptor | | | | | | | |
|---|---|---|---|---|---|---|---|---|---|
| | | $\alpha_1$ | $\alpha_{2C}$ | $CB_1$ | $D_3$ | $H_1$ | $5\text{-}HT_{1B}$ | $5\text{-}HT_{2B}$ | $5\text{-}HT_{5A}$ |
| 4 | $10^{-6}$ | 5 | 9 | 8 | 8 | 6 | 24 | 93 | 9 |
|   | $10^{-8}$ | ND | ND | ND | ND | ND | ND | 6 | ND |
| 14 | $10^{-6}$ | ND | ND | ND | ND | ND | 40 | 87 | 7 |
|   | $10^{-8}$ | ND | ND | ND | ND | ND | ND | 7 | ND |

ND = not determined

REFERENCES

[1] Aghajanian, G. K.; Sanders-Bush, E. in *Neuropsychopharmacology—The fifth generation of progress*; Davis, K. L., Charney, D., Coyle, J. T., Nemeroff, C., Eds.; Lippincott, Williams&Wilkins: New York, 2002,

[2] Ruat, M.; Traiffort, E.; Leurs, R.; Tardivel-Lacombe, J.; Diaz, J.; Arrang, J. M.; Schwartz, J. C. *Proc. Natl. Acad. Sci. U.S.A.* 1993, 90, 8547-8551,

[3] Lovenberg, T. W.; Baron, B. M.; Delecea, L.; Miller, J. D.; Prosser, R. A.; Rea, M. A.; Foye, P. E.; Racke, M.; Slone, A. L.; Siegel, B. W. *Neuron.* 1993, 11, 449-458,

[4] Bard, J. A.; Zgombick, J.; Adham, N.; Vaysse, P.; Branchek, T. A.; Weinshank, R. L. *J. Biol. Chem.* 1993, 268, 23422-23426,

[5] Hedlund, P. B.; Sutcliffe, J. G. *Trends Pharmacol. Sci.* 2004, 25, 481-486,

[6] Naumenko, V. S.; Popova, N. K.; Lacivita, E.; Leopoldo, M.; Ponimaskin, E. G. CNS *Neurosci Ther.* 2004, 20, 582-90,

[7] Roberts, A. J.; Krucker, T.; Levy, C. L.; Slanina, K. A.; Sutcliffe, J. G.; Hedlund, P. B. *Eur. J. Neurosci.* 2004, 19, 1913-1922,

[8] Gasbarri, A.; Cifariello, A.; Pompili, A.; Meneses, A. *Behav. Brain Res.* 2008, 195, 164-170,

[9] Eriksson, T. M.; Golkar, A.; Ekstrom, J. C.; Svenningsson, P.; Ogren, S. O. *Eur. J. Pharmacol.* 2008, 596, 107-110,

[10] Sarkisyan, G.; Hedlund, P. B. *Behav. Brain Res.* 2009, 202, 26-31,

[11] Meneses, A.; Perez-Garcia, G.; Liy-Salmeron, G.; Flores-Galvez, D.; Castillo, C.; Castillo, E. *Behav. Brain Res.* 2008, 195, 112-119,

[12] Hedlund, P. B.; Sutcliffe, J. G. *Trends Pharmacol. Sci.* 2004, 25, 481-486,

[13] Matthys, A.; Haegeman, G.; Van Craenenbroeck, K.; Vanhoenacker, P. *Mol. Neurobiol.* 2011, 43, 228-253,

[14] Di Pilato, P.; Niso, M.; Adriani, W.; Romano, E.; Travaglini, D.; Berardi, F.; Colabufo, N. A.; Perrone, R.; Laviola, G.; Lacivita, E.; Leopoldo, M. *Rev. Neurosci.* 2014, 25, 401-415,

[15] Bento, A. P.; Gaulton, A.; Hersey, A.; Bellis, L. J.; Chambers, J.; Davies, M.; Kruger, M. A.; Light, Y.; Mak, L.; McGlinchey, S.; Nowotka, M.; Papadatos, G.; Santos, R.; Overington, J. P. *Nucleic Acids Res.* 2014, 42, 1083-1090,

[16] Sleight, A. J.; Carolo, C.; Petit, N.; Zwingelstein, C.; Bourson, A. *Mol Pharm.* 1995, 47, 99-103,

[17] Mnie-Filali, O.; Lambás-Señas, L.; Zimmer, L.; Haddjeri. N. *Drug News Perspect.* 2007, 20, 613-618,

[18] Hagan, J. J.; Price, G. W.; Jeffrey, P.; Deeks, N. J.; Stean, T.; Piper, D.; Smith, M. I.; Upton, N.; Medhurst, A. D.; Middlemiss, D. N.; Riley, G. J.; Lovell, P. J.; Bromidge, S. M.; Thomas, D. R. *Br. J. Pharmacol.* 2000, 130, 539-548,

[19] Shapiro, D. A.; Renock, S.; Arrington, E.; Chiodo, L. A.; Liu, L. X.; Sibley, D. R.; Roth, B. L.; Mailman, R. *Neuropsychopharmacology.* 2003, 28, 1400-1411,

[20] Brenchat, A.; Romero, L.; García, M.; Pujol, M.; Bugueño, J.; Torrens, A.; Hamon, M.; Baeyens, J. M.; Buschmann, H.; Zamanillo, D. *Pain,* 2009, 141, 239-247,

[21] Thomson, C. G.; Beer, M. S.; Curtis, N. R.; Diggle, H. J.; Handford, E.; Kulagowski, J. *J. Bioorg. Med. Chem. Lett.* 2004, 14, 677-680,

[22] Leopoldo, M.; Lacivita, E.; Contino, M.; Colabufo, N. A.; Berardi, F.; Perrone, R. *J. Med. Chem.* 2007, 50, 4214-4221,

[23] Leopoldo, M.; Berardi, F.; Colabufo, N. A.; Contino, M.; Lacivita, E.; Niso, M; Perrone, R.; Tortorella, V. *J. Med. Chem.* 2004, 47, 6616-6624.

[24] Leopoldo, M.; Lacivita, E.; De Giorgio, P.; Fracasso, C.; Guzzetti, S.; Caccia, S.; Contino, M.; Colabufo, N. A.; Berardi, F.; Perrone, R. *J. Med. Chem.* 2008, 51, 5813-5822,

[25] Hedlund, P. B.; Leopoldo, M.; Caccia, S.; Sarkisyan, G.; Fracasso, C.; Martelli, G.; Lacivita, E.; Berardi, F.; Perrone, R. *Neurosci Lett.* 2010, 481, 12-16,

[26] Powell, S. L.; Goedecke, T.; Nicolic, D.; Chen, S. N.; Ahn, S.; Dietz, B.; Farnsworth, N. R.; Van Breemen, R. B.; Lankin, D. C.; Pauli, G. F.; Bolton, J. L. *J. Agric. Food Chem.* 2008, 56, 11718-11726,

[27] Bosker, F. J.; Folgering, J. H.; Gladkevich, A. V.; Schmidt, A.; Van Der Hart, M. C.; Sprouse, J.; den Boer, J. A.; Westerink, B. H.; Cremers, T. I. *J. Neurochem.* 2009, 108, 1126-1135,

[28] Tiwari, A. K.; Yui, J.; Pooja; Aggarwal, S.; Yamasaki, T.; Xie, L.; Chadh, N.; Zhang, Y.; Fujinaga, M.; Shimoda, Y.; Kumata, K.; Mishra, A. K.; Ogawaac, M.; Zhang, M-R. *RSC Adv.* 2015, 5, 19752-19759,

[29] Canese, R.; Zoratto, F.; Altabella, L.; Porcari, P.; Mercurio, L.; de Pasquale, F.; Butti, E.; Martino, G.; Lacivita, E.; Leopoldo, M.; Laviola, G.; Adriani, W. *Psychopharmacology (Berl),* 2015, 232, 75-89,

[30] De Filippis, B.; Chiodi, V.; Adriani, W.; Lacivita, E.; Mallozzi. C.; Leopoldo, M.; Domenici, M. R.; Fuso, A.; Laviola G. *Front. Behav. Neurosci.,* 2015, 9:86,

[31] D. Costa, L.; Spatuzza, M.; D'Antoni, S.; Bonaccorso, C. M.; Trovato, C.; Musumeci, S. A.; Leopoldo, M.; Lacivita, E.; Catania, M. V.; Ciranna, L. *Biol. Psychiatry,* 2012, 72, 924-933,

[32] Clark, T.; Hennemann, M.; Murray, J. S.; Politzer, P. *J. Mol. Model.* 2007, 13 (2), 291-296,

[33] Clark, T. Rev. *Comput. Mol. Sci.* 2012, 3 (1), 1-8,

[34] Wilcken, R.; Zimmermann, M. O.; Lange, A.; Joerger, A. C.; Boeckler, F. M. *J. Med. Chem* 2013, 56 (4), 1363-1388,

[35] Agarwal, A.; Jalluri, R. K.; DeWitt Blanton Jr., C.; Taylor, W. *Synthetic Communications* 2006, 23, 1101-1110,

[36] Cheng Y.; Prusoff W. *Biochem. Pharmacol.*, 1973, 22, 3099-3108,

[37] Zajdel P, Kurczab R, Grychowska K, Satafa G, Pawlowski M, Bojarski A J. *Eur J Med Chem.* 2012, 56, 348-60,

[38] Deau E.; Robin E.; Voinea R.; Percina N; Satafa G.; Finaru A.-L.; Chartier A.; Tamagnan G.; Alagille D.; Bojarski A. J.; Morisset-Lopez S.; Suzenet F.; Guillaumet G. *J. Med. Chem.* 2015, 58, 8066-8096,

[39] Greengrass, P.; Bremner, R. *Eur. J. Pharmacol.* 1979, 55, 323-326,

[40] Devedjian, J. C; Esclapez, F.; Denis-Pouxviel, C.; Paris, H. *Eur. J. Pharmacol.* 1994, 252, 43-49,

[41] Rinaldi-Carmona, M.; Calandra, B.; Shire, D.; Bouaboula, M.; Oustric, D.; Barth, F.; Casellas, P.; Ferrara, P.; Le Fur, G. *J. Pharmacol. Exp. Ther.* 1996, 278, 871-878,

[42] Mackenzie, R. G.; VanLeeuwen, D.; Pugsley, T. A.; Shih, Y. H.; Demattos, S.; Tang, L.; Todd, R. D.; O'Malley, K. L. *Eur. J. Pharmacol.* 1994, 266, 79-85,

[43] Smit, M. J.; Timmerman, H.; Hijzelendoorn, J. C.; Fukui, H.; Leurs, R. *Brit. J. Pharmacol.* 1996, 117, 1071-1080,

[44] Hoyer, D.; Engel, G.; Kalkman, H. O. *Eur. J. Pharmacol.* 1985, 118, 1-12,

[45] Choi, D. S.; Birraux, G.; Launay, J. M.; Maroteaux, L. *FEBS Lett.* 1994, 352, 393-399,

[46] Rees, S.; den Daas, I.; Foord, S.; Goodson, S.; Bull, D.; Kilpatrick, G.; Lee, M. *FEBS Lett.* 1994, 355, 242-246,

[47] Wager, T. T.; Hou X.; Verhoest P., R.; Villalobos A., *ACS Chem. Neurosci.* 2010, 1, 435-449.

The invention claimed is:

1. A substituted indole derivative of Formula (I),

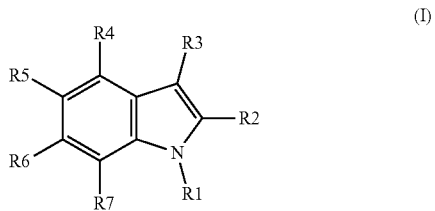

(I)

wherein:
R1 represents hydrogen;
R2 represents hydrogen; and
R3 represents the substituted imidazol-5-yl of Formula (II)

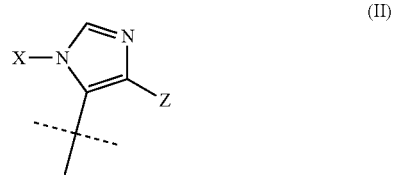

(II)

wherein:
X represents hydrogen, $C_1$-$C_6$ alkyl, $C_3$ cycloalkyl, $C_2$-$C_4$ alkenyl, $C_1$-$C_4$ alkoxy, methoxy-$C_1$-$C_4$ alkyl, $C_6$-$C_{10}$ aryl, or $C_6$-$C_{10}$ aryl-$C_1$-$C_4$ alkyl; and
Z represents hydrogen;
R4 represents hydrogen, halogen, or methoxy;
R5 represents hydrogen, halogen, methyl, hydroxy, methoxy, benzyloxy, cyano, or amido;
R6 represents hydrogen or bromine;
R7 represents hydrogen, fluorine, or methyl; and
wherein the halogen is selected from fluorine, chlorine, bromine, and iodine;
or its stereoisomers, mixtures of stereoisomers in any proportions, tautomers, solvates hydrates, or pharmaceutically acceptable salts thereof, with the proviso that the substituted indole derivative of Formula (I) is
neither 3-(1H-imidazol-5-yl)-1H-indole
nor 3-(1-methyl-1H-imidazol-5-yl)-1H-indole.

2. The compound for use according to claim 1, wherein:
R1 represents hydrogen;
R2 represents hydrogen;
R3 represents the substituted imidazol-5-yl of Formula (II) as defined in claim 1, wherein:
X represents hydrogen, $C_1$-$C_6$ alkyl, $C_3$ cycloalkyl, $C_2$-$C_4$ alkenyl, $C_1$-$C_4$ alkoxy, methoxy-$C_1$-$C_4$ alkyl, $C_6$-$C_{10}$ aryl, or $C_6$-$C_{10}$ aryl-$C_1$-$C_4$ alkyl; and
Z represents hydrogen;
R4 represents hydrogen, bromine, or methoxy;
R5 represents hydrogen, halogen, methyl, hydroxy, methoxy, benzyloxy, cyano, or amido;
R6 represents hydrogen or bromine; and
R7 represents hydrogen, fluorine, or methyl;
or a pharmaceutically acceptable salt thereof.

3. The compound according to claim 1, selected from the group consisting of:
5-methoxy-3-(1-methyl-1H-imidazol-5-yl)-1H-indole;
3-(1-ethyl-1H-imidazol-5-yl)-5-methoxy-1H-indole;
3-(1-propyl-1H-imidazol-5-yl)-5-methoxy-1H-indole;
3-(1-butyl-1H-imidazol-5-yl)-5-methoxy-1H-indole;
3-(1-cyclopropyl-1H-imidazol-5-yl)-5-methoxy-1H-indole;
5-methoxy-3-[1-(prop-2-en-1-yl)-1H-imidazol-5-yl]-1H-indole;
4-bromo-3-(1-ethyl-1H-imidazol-5-yl)-1H-indole;
3-(1-ethyl-1H-imidazol-5-yl)-5-fluoro-1H-indole;
5-chloro-3-(1-ethyl-1H-imidazol-5-yl)-1H-indole;
5-bromo-3-(1-ethyl-1H-imidazol-5-yl)-1H-indole;
5-iodo-3-(1-ethyl-1H-imidazol-5-yl)-1H-indole;
3-(1-ethyl-1H-imidazol-5-yl)-1H-indole-5-carbonitrile;
3-(1-ethyl-1H-imidazol-5-yl)-5-methyl-1H-indole;
3-(1-ethyl-1H-imidazol-5-yl)-1H-indol-5-ol;
3-(1-ethyl-1H-imidazol-5-yl)-4-methoxy-1H-indole;
3-(1-ethyl-1H-imidazol-5-yl)-7-methyl-1H-indole;
3-(1-ethyl-1H-imidazol-5-yl)-1H-indole;
5-methoxy-3-[1-(3-methoxypropyl)-1H-imidazol-5-yl]-1H-indole;
5-benzyloxy-3-(1-ethyl-1H-imidazol-5-yl)-1H-indole;
3-(1-ethyl-1H-imidazol-5-yl)-7-fluoro-5-iodo-1H-indole;
3-(1-ethyl-1H-imidazol-5-yl)-1H-indole-5-carboxamide;
3-(1-cyclopropyl-1H-imidazol-5-yl)-5-iodo-1H-indole;
5-methoxy-3-[1-(2-phenylethyl)-1H-imidazol-5-yl]-1H-indole; or
a pharmaceutically acceptable salt thereof.

4. The compound according to claim 1, selected from the group consisting of:
5-methoxy-3-(1-methyl-1H-imidazol-5-yl)-1H-indole;
3-(1-ethyl- 1H-imidazol-5-yl)-5-methoxy-1H-indole;
5-methoxy-3-(1-propyl-1H-imidazol-5-yl)-1H-indole;

5-chloro-3-(1-ethyl-1H-imidazol-5-yl)-1H-indole;
5-bromo-3-(1-ethyl-1H-imidazol-5-yl)-1H-indole;
3-(1-ethyl-1H-imidazol-5-yl)-5-iodo-1H-indole;
3-(1-ethyl-1H-imidazol-5-yl)-5-methyl-1H-indole;
3-(1-ethyl-1H-imidazol-5-yl)-1H-indol-5-ol;
3-(1-ethyl-1H-imidazol-5-yl)-7-fluoro-5-iodo-1H-indole; and
3-(1-ethyl-1H-imidazol-5-yl)-1H-indole-5-carboxamide; or
a pharmaceutically acceptable salt thereof.

5. The compound according to claim 1, selected from the group consisting of:
4-fluoro-5-iodo-3-(1-methyl-1H-imidazol-5-yl)-1H-indole;
3-(1-ethyl-1H-imidazol-5-yl)-4-fluoro-5-iodo-1H-indole;
5-bromo-3-(1-ethyl-1H-imidazol-5-yl)-4-fluoro-1H-indole;
3-(1-ethyl-1H-imidazol-5-yl)-4-fluoro-1H-indole-5-carboxamide;
4-fluoro-3-(1-methyl-1H-imidazol-5-yl)-1H-indole-5-carboxamide; and
4-fluoro-3-(1-ethyl-1H-imidazol-5-yl)-1H-indole; or
a pharmaceutically acceptable salt thereof.

6. A pharmaceutical composition comprising a therapeutically effective amount of one or more compounds as claimed in claim 1 as an active component, and one or more pharmaceutical excipients.

7. The pharmaceutical composition according to claim 6, to be administered orally, parenterally, by inhalation, transdermally, or transmucosally.

8. The pharmaceutical composition according to claim 6, further comprising a 5-HT$_7$-active component selected from the group consisting of aripiprazole, amisulpride, chlorpromazine, clozapine, risperidone, ziprasidone, fluoxetine, 5-CT, 5-methoxytryptamine, 8-OH-DPAT, aripiprazole, AS-19, E-55888, MSD-5a, LP-12, LP-44, LP-211, RA-7, and N$^\omega$-methylserotonin.

9. A method of treating a disease or disorder mediated by 5-HT$_7$ serotonin receptor in a mammal, wherein the disease or disorder is selected from Rett syndrome, Fragile X syndrome, mood disorders, depression, anxiety, sleep disorders, gut disorders, pain, schizophrenia, inflammatory processes in the CNS, dementia, Alzheimer's disease, autistic disorder and other neuropsychiatric disorders, the method comprising administering to said mammal suffering from the disease or disorder a therapeutically effective amount of the compound of claim 1.

* * * * *